ically, cen screening and therapeutic methods utilizing compositions of

(12) United States Patent
Busfield

(10) Patent No.: US 6,287,808 B1
(45) Date of Patent: Sep. 11, 2001

(54) MOLECULES OF THE HERPESVIRUS-ENTRY-MEDIATOR-RELATED PROTEIN FAMILY AND USES THEREOF

(75) Inventor: Samantha J. Busfield, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/146,950

(22) Filed: Sep. 3, 1998

(51) Int. Cl.[7] .............................. C12N 15/12; C12N 5/10; C12N 16/63
(52) U.S. Cl. .................... 435/69.1; 536/23.5; 536/24.31; 435/320.1; 435/252.3; 435/325
(58) Field of Search ................................ 536/23.5, 24.31; 435/320.1, 325, 252.3, 366, 69.1

(56) References Cited

FOREIGN PATENT DOCUMENTS

| WO 96/34095 | 10/1996 | (WO) . |
| WO 97/04658 | 2/1997 | (WO) . |
| WO 98/18824 | 5/1998 | (WO) . |

OTHER PUBLICATIONS

Gruss, "Molecular, structural, and biological characteristics of the tumor necrosis factor ligand super–family" Int J. Clin Lab Res 26:143–159 (1996).

Montgomery et al., "Herpes Simplex Virus–1 Entry into Cells Mediated by a Novel Member of the TNF/NGF Receptor Family" Cell, 87:427–436 (1996).

Whitbeck et al., "Glycoprotein D of Herpes Simplex Virus (HSV) Binds Directly to HVEM, a Member of the Tumor Necrosis Factor Receptor Superfamily and a Mediator of HSV Entry" Journal of Virology, 71:6083–6093 (1997).

Marsters et al., "Herpesvirus Entry Mediator, a Member of the Tumor Necrosis Factor Receptor (TNFR) Family, Interacts with Members of the TNFR–associated Factor Family and Activates the Transcription Factors NF–χB and AP–1*" The Journal of Biological Chemistry 272:14029–14032 (1997).

*Primary Examiner*—Mary E. Mosher
(74) *Attorney, Agent, or Firm*—Fish & Richardson, P.C.

(57) ABSTRACT

Novel TANGO-69-receptor polypeptides, proteins, and nucleic acid molecules are disclosed. In addition to isolated, full-length TANGO-69-receptor proteins, the invention further provides isolated TANGO-69-receptor fusion proteins, antigenic peptides and anti-TANGO-69-receptor antibodies. The invention also provides TANGO-69-receptor nucleic acid molecules, recombinant expression vectors containing a nucleic acid molecule of the invention, host cells into which the expression vectors have been introduced and non-human transgenic animals in which a TANGO-69-receptor gene has been introduced or disrupted. Diagnostic, screening and therapeutic methods utilizing compositions of the invention are also provided.

17 Claims, 13 Drawing Sheets

```
   1 GTCGACCCACGCGTCCGCTCGGCTTTGCCTGGACAGCTCCTGCCTCCCGCAGGGCCCACC
  61 TGTGTCCCCCAGCGCCGCTCCACCCAGCAGGCCTGAGCCCCTCTCTGCTGCCAGACACCC
 121 CCTGCTGCCCACTCTCCTGCTGCTCGGGTTCTGAGGCACAGCTTGTCACACCGAGGCGGA
 181 TTCTCTTTCTCTTTCTCTTTCTCTTCTGGCCCACAGCCGCAGCAATGGCGCTGAGTTCCT

241 CTGCTGGAGTTCATCCTGCTAGCTGGGTTCCCGAGCTGCCGGTCTGAGCCTGAGGCATGG
   1                                                          M  E

301 AGCCTCCTGGAGACTGGGGGCCTCCTCCCTGGAGATCCACCCCCAGAACCGACGTCTTGA
   3   P  P  G  D  W  G  P  P  P  W  R  S  T  P  R  T  D  V  L  R

361 GGCTGGTGCTGTATCTCACCTTCCTGGGAGCCCCCTGCTACGCCCCAGCTCTGCCGTCCT
  23   L  V  L  Y  L  T  F  L  G  A  P  C  Y  A  P  A  L  P  S  C

421 GCAAGGAGGACGAGTACCCAGTGGGCTCCGAGTGCTGCCCCAAGTGCAGTCCAGGTTATC
  43   K  E  D  E  Y  P  V  G  S  E  C  C  P  K  C  S  P  G  Y  R

481 GTGTGAAGGAGGCCTGCGGGGAGCTGACGGGCACAGTGTGTGAACCCTGCCCTCCAGGCA
  63   V  K  E  A  C  G  E  L  T  G  T  V  C  E  P  C  P  P  G  T

541 CCTACATTGCCCACCTCAATGGCCTAAGCAAGTGTCTGCAGTGCCAAATGTGTGACCCAG
  83   Y  I  A  H  L  N  G  L  S  K  C  L  Q  C  Q  M  C  D  P  A

601 CCATGGGCCTGCGCGCGAGCCGGAACTGCTCCAGGACAGAGAACGCCGTGTGTGGCTGCA
 103   M  G  L  R  A  S  R  N  C  S  R  T  E  N  A  V  C  G  C  S

661 GCCCAGGCCACTTCTGCATCGTCCAGGACGGGGACCACTGCGCCGCGTGCCGCGCTTACG
 123   P  G  H  F  C  I  V  Q  D  G  D  H  C  A  A  C  R  A  Y  A

721 CCACCTCCAGCCCGGGCCAGAGGGTGCAGAAGGGAGGCACCGAGAGTCAGGACACCCTGT
 143   T  S  S  P  G  Q  R  V  Q  K  G  G  T  E  S  Q  D  T  L  C

781 GTCAGAACTGCCCCCCGGGGACCTTCTCTCCCAATGGGACCCTGGAGGAATGTCAGCACC
 163   Q  N  C  P  P  G  T  F  S  P  N  G  T  L  E  E  C  Q  H  Q

841 AGACCAACCGAGCTTGGAAAAGTCAGACAGACCTCTGAGGTCTCATCCTGGAGCTGCCAC
 183   T  N  R  A  W  K  S  Q  T  D  L  *

901 CAGCCCAGCCTCCCTGGGACCTGTCTTCACTGCCTGGGGCCCTGGGAGCCAGGGAGGCTC
 961 CCTGAGGCTGAGTGAACACTGGGCGCTGCACCTGCCTCTCCCACGTCCTCGGCCCCACTC
1021 CCGCAGGTGCAGCTGGCTGGTGACGAAGGCCGGAGCTGGGACCAGCAGCTCCCACTGGGT
1081 ATGGTGGTTTCTCTCAGGGAGCCTCGTCATCGTCATTGTTTGCTCCACAGTTGGCCTAAT
1141 CATATGTGTGAAAAGAAGAAAGCCAAGGGGTGATGTAGTCAAGGTGATCGTCTCCATCCA
1201 GCGGAAAAGACAGGAGGCAGAAGGTGAGGCCACAGTCATTGAGGCCCTGCAGGCCCCTCC
1261 GGACGTCACCACGGTGGCCGTGGAGGAGACAATACCCTCATTCACGGGGAGGAGCCCAAA
1321 CCACTGACCCACAGACTCTGCACCCCGACGCCAGAGATACCTGGAGCGACGGCTGCTGAA
1381 AGAGGCTGTCCACCTGGCGAAACCACCGGAGCCCGGAGGCTTGGGGGCTCCGCCCTGGGC
1441 TGGCTTCCGTCTCCTCCAGTGGAGGGAGAGGTGGGGCCCCTGCTGGGGTAGAGCTGGGGA
1501 CGCCACGTGCCATTCCCATGGGCCAGTGAGGGCCTGGGGCCTCTGTTCTGCTGTGGCCTG
1561 AGCTCCCCAGAGTCCTGAGGAGGAGCGCCAGTTGCCCCTCGCTCACAGACCACACACCCA
1621 GCCCTCCTGGGCCAGCCCAGAGGGCCCTTCAGACCCCAGCTGTCTGCGCGTCTGACTCTT
1681 GTGGCCTCAGCAGGACAGGCCCCGGGCACTGCCTCACAGCCAAGGCTGGACTGGGTTGGC
1741 TGCAGTGTGGTGTTTAGTGGATACCACATCGGAAGTGATTTTCTAAATTGGATTTGAATT
1801 CGGCTCCTGTTTTCTATTTGTCATGAAACAGTGTATTTGGGGAGATGCTGTGGGAGGATG
1861 TAAATATCTTGTTTCTCCTCAAAAAAAAAAAAAAAAAAAAAAAAAAAAAAAAAAAAAAAA
1921 AAAAAAAA
```

FIG. 1

```
            10        20        30        40        50        60
HVEM    CCTTCATACCGGCCCTTCCCCTCGGCTTTGCCTGGACAGCTCCTGCCTCCCGCAGGGCCC
        ::. ::: .: : ::: ::::::::::::::::::::::::::::::::::::::::::
SHVEM   --GTCG-ACCCACGCGTCCGCTCGGCTTTGCCTGGACAGCTCCTGCCTCCCGCAGGGCCC
                  10        20        30        40        50

70        80        90       100       110       120
HVEM    ACCTGTGTCCCCAGCGCCGCTCCACCCAGCAGGCCTGAGCCCCTCTCTGCTGCCAGACA
        ::::::::::::::::::::::::::::::::::::::::::::::::::::::::::
SHVEM   ACCTGTGTCCCCAGCGCCGCTCCACCCAGCAGGCCTGAGCCCCTCTCTGCTGCCAGACA
            60        70        80        90       100       110

130       140       150       160       170       180
HVEM    CCCCCTGCTGCCCACTCTCCTGCTGCTCGGGTTCTGAGGCACAGCTTGTCACACCGAGGC
        ::::::::::::::::::::::::::::::::::::::::::::::::::::::::::::
SHVEM   CCCCCTGCTGCCCACTCTCCTGCTGCTCGGGTTCTGAGGCACAGCTTGTCACACCGAGGC
           120       130       140       150       160       170

190       200       210       220       230
HVEM    GGATTCTCTTTCTCTTTCTCTT------CTGGCCCACAGCCGCAGCAATGGCGCTGAGTT
        :::::::::::::::::::::       ::::::::::::::::::::::::::::::::
SHVEM   GGATTCTCTTTCTCTTTCTCTTTCTCTTCTGGCCCACAGCCGCAGCAATGGCGCTGAGTT
           180       190       200       210       220       230

240       250       260       270       280       290
HVEM    CCTCTGCTGGAGTTCATCCTGCTAGCTGGGTTCCCGAGCTGCCGGTCTGAGCCTGAGGCA
        ::::::::::::::::::::::::::::::::::::::::::::::::::::::::::::
SHVEM   CCTCTGCTGGAGTTCATCCTGCTAGCTGGGTTCCCGAGCTGCCGGTCTGAGCCTGAGGCA
           240       250       260       270       280       290

300       310       320       330       340       350
HVEM    TGGAGCCTCCTGGAGACTGGGGGCCTCCTCCCTGGAGATCCACCCCCAGAACCGACGTCT
        ::::::::::::::::::::::::::::::::::::::::::::::::::::::::::::
SHVEM   TGGAGCCTCCTGGAGACTGGGGGCCTCCTCCCTGGAGATCCACCCCCAGAACCGACGTCT
           300       310       320       330       340       350

360       370       380       390       400       410
HVEM    TGAGGCTGGTGCTGTATCTCACCTTCCTGGGAGCCCCCTGCTACGCCCCAGCTCTGCCGT
        ::::::::::::::::::::::::::::::::::::::::::::::::::::::::::::
SHVEM   TGAGGCTGGTGCTGTATCTCACCTTCCTGGGAGCCCCCTGCTACGCCCCAGCTCTGCCGT
           360       370       380       390       400       410
```

FIG. 2A

```
             420        430        440        450        460        470
HVEM    CCTGCAAGGAGGACGAGTACCCAGTGGGCTCCGAGTGCTGCCCCAAGTGCAGTCCAGGTT
        ::::::::::::::::::::::::::::::::::::::::::::::::::::::::::::
SHVEM   CCTGCAAGGAGGACGAGTACCCAGTGGGCTCCGAGTGCTGCCCCAAGTGCAGTCCAGGTT
             420        430        440        450        460        470

480        490        500        510        520        530
HVEM    ATCGTGTGAAGGAGGCCTGCGGGGAGCTGACGGGCACAGTGTGTGAACCCTGCCCTCCAG
        ::::::::::::::::::::::::::::::::::::::::::::::::::::::::::::
SHVEM   ATCGTGTGAAGGAGGCCTGCGGGGAGCTGACGGGCACAGTGTGTGAACCCTGCCCTCCAG
             480        490        500        510        520        530

540        550        560        570        580        590
HVEM    GCACCTACATTGCCCACCTCAATGGCCTAAGCAAGTGTCTGCAGTGCCAAATGTGTGACC
        ::::::::::::::::::::::::::::::::::::::::::::::::::::::::::::
SHVEM   GCACCTACATTGCCCACCTCAATGGCCTAAGCAAGTGTCTGCAGTGCCAAATGTGTGACC
             540        550        560        570        580        590

600        610        620        630        640        650
HVEM    CAGCCATGGGCCTGCGCGCGAGCCGGAACTGCTCCAGGACAGAGAACGCCGTGTGTGGCT
        ::::::::::::::::::::::::::::::::::::::::::::::::::::::::::::
SHVEM   CAGCCATGGGCCTGCGCGCGAGCCGGAACTGCTCCAGGACAGAGAACGCCGTGTGTGGCT
             600        610        620        630        640        650

660        670        680        690        700        710
HVEM    GCAGCCCAGGCCACTTCTGCATCGTCCAGGACGGGGACCACTGCGCCGCGTGCCGCGCTT
        ::::::::::::::::::::::::::::::::::::::::::::::::::::::::::::
SHVEM   GCAGCCCAGGCCACTTCTGCATCGTCCAGGACGGGGACCACTGCGCCGCGTGCCGCGCTT
             660        670        680        690        700        710

720        730        740        750        760        770
HVEM    ACGCCACCTCCAGCCCGGGCCAGAGGGTGCAGAAGGGAGGCACCGAGAGTCAGGACACCC
        ::::::::::::::::::::::::::::::::::::::::::::::::::::::::::::
SHVEM   ACGCCACCTCCAGCCCGGGCCAGAGGGTGCAGAAGGGAGGCACCGAGAGTCAGGACACCC
             720        730        740        750        760        770

780        790        800        810        820        830
HVEM    TGTGTCAGAACTGCCCCCCGGGGACCTTCTCTCCCAATGGGACCCTGGAGGAATGTCAGC
        ::::::::::::::::::::::::::::::::::::::::::::::::::::::::::::
SHVEM   TGTGTCAGAACTGCCCCCCGGGGACCTTCTCTCCCAATGGGACCCTGGAGGAATGTCAGC
             780        790        800        810        820        830

840
HVEM    ACCAGACCAA--------------------------------------------------
        ::::::::::
SHVEM   ACCAGACCAACCGAGCTTGGAAAAGTCAGACAGACCTCTGAGGTCTCATCCTGGAGCTGC
             840        850        860        870        880        890

HVEM    ------------------------------------------------------------
```

FIG. 2B

```
SHVEM   CACCAGCCCAGCCTCCCTGGGACCTGTCTTCACTGCCTGGGGCCCTGGGAGCCAGGGAGG
        900       910       920       930       940       950

HVEM    ------------------------------------------------------------

SHVEM   CTCCCTGAGGCTGAGTGAACACTGGGCGCTGCACCTGCCTCTCCCACGTCCTCGGCCCCA
        960       970       980       990       1000      1010

850       860       870       880       890
HVEM    --------GTGCAGCTGGCTGGTGACGAAGGCCGGAGCTGGGACCAGCAGCTCCCACTG
                ::::::::::::::::::::::::::::::::::::::::::::::::::::
SHVEM   CTCCCGCAGGTGCAGCTGGCTGGTGACGAAGGCCGGAGCTGGGACCAGCAGCTCCCACTG
        1020      1030      1040      1050      1060      1070

900       910       920       930       940       950
HVEM    GGTATGGTGGTTTCTCTCAGGGAGCCTCGTCATCGTCATTGTTTGCTCCACAGTTGGCCT
        ::::::::::::::::::::::::::::::::::::::::::::::::::::::::::::
SHVEM   GGTATGGTGGTTTCTCTCAGGGAGCCTCGTCATCGTCATTGTTTGCTCCACAGTTGGCCT
        1080      1090      1100      1110      1120      1130

960       970       980       990       1000      1010
HVEM    AATCATATGTGTGAAAAGAAGAAAGCCAAGGGGTGATGTAGTCAAGGTGATCGTCTCCGT
        ::::::::::::::::::::::::::::::::::::::::::::::::::::::::::.:
SHVEM   AATCATATGTGTGAAAAGAAGAAAGCCAAGGGGTGATGTAGTCAAGGTGATCGTCTCCAT
        1140      1150      1160      1170      1180      1190

1020      1030      1040      1050      1060      1070
HVEM    CCAGCGGAAAAGACAGGAGGCAGAAGGTGAGGCCACAGTCATTGAGGCCCTGCAGGCCCC
        ::::::::::::::::::::::::::::::::::::::::::::::::::::::::::::
SHVEM   CCAGCGGAAAAGACAGGAGGCAGAAGGTGAGGCCACAGTCATTGAGGCCCTGCAGGCCCC
        1200      1210      1220      1230      1240      1250

1080      1090      1100      1110      1120      1130
HVEM    TCCGGACGTCACCACGGTGGCCGTGGAGGAGACAATACCCTCATTCACGGGGAGGAGCCC
        ::::::::::::::::::::::::::::::::::::::::::::::::::::::::::::
SHVEM   TCCGGACGTCACCACGGTGGCCGTGGAGGAGACAATACCCTCATTCACGGGGAGGAGCCC
        1260      1270      1280      1290      1300      1310

1140      1150      1160      1170      1180      1190
HVEM    AAACCACTGACCCACAGACTCTGCACCCCGACGCCAGAGATACCTGGAGCGACGGCTGCT
        ::::::::::::::::::::::::::::::::::::::::::::::::::::::::::::
SHVEM   AAACCACTGACCCACAGACTCTGCACCCCGACGCCAGAGATACCTGGAGCGACGGCTGCT
        1320      1330      1340      1350      1360      1370

1200      1210      1220      1230      1240      1250
HVEM    GAAAGAGGCTGTCCACCTGGCGAAACCACCGGAGCCCGGAGGCTTGGGGGCTCCGCCCTG
        ::::::::::::::::::::::::::::::::::::::::::::::::::::::::::::
SHVEM   GAAAGAGGCTGTCCACCTGGCGAAACCACCGGAGCCCGGAGGCTTGGGGGCTCCGCCCTG
        1380      1390      1400      1410      1420      1430

1260      1270      1280      1290      1300      1310
HVEM    GGCTGGCTTCCGTCTCCTCCAGTGGAGGGAGAGGTGGGGCCCCTGCTGGGGTAGAGCTGG
        ::::::::::::::::::::::::::::::::::::::::::::::::::::::::::::
```

FIG. 2C

```
SHVEM  GGCTGGCTTCCGTCTCCTCCAGTGGAGGGAGAGGTGGGGCCCCTGCTGGGGTAGAGCTGG
           1440      1450      1460      1470      1480      1490

1320      1330      1340      1350      1360      1370
HVEM   GGACGCCACGTGCCATTCCCATGGGCCAGTGAGGGCCTGGGGCCTCTGTTCTGCTGTGGC
       ::::::::::::::::::::::::::::::::::::::::::::::::::::::::::::
SHVEM  GGACGCCACGTGCCATTCCCATGGGCCAGTGAGGGCCTGGGGCCTCTGTTCTGCTGTGGC
           1500      1510      1520      1530      1540      1550

1380      1390      1400      1410      1420      1430
HVEM   CTGAGCTCCCCAGAGTCCTGAGGAGGAGCGCCAGTTGCCCCTCGCTCACAGACCACACAC
       ::::::::::::::::::::::::::::::::::::::::::::::::::::::::::::
SHVEM  CTGAGCTCCCCAGAGTCCTGAGGAGGAGCGCCAGTTGCCCCTCGCTCACAGACCACACAC
           1560      1570      1580      1590      1600      1610

1440      1450      1460      1470      1480      1490
HVEM   CCAGCCCTCCTGGGCCAGCCCAGAGGGCCCTTCAGACCCCAGCTGTCTGCGCGTCTGACT
       ::::::::::::::::::::::::::::::::::::::::::::::::::::::::::::
SHVEM  CCAGCCCTCCTGGGCCAGCCCAGAGGGCCCTTCAGACCCCAGCTGTCTGCGCGTCTGACT
           1620      1630      1640      1650      1660      1670

1500      1510      1520      1530      1540      1550
HVEM   CTTGTGGCCTCAGCAGGACAGGCCCCGGGCACTGCCTCACAGCCAAGGCTGGACTGGGTT
       ::::::::::::::::::::::::::::::::::::::::::::::::::::::::::::
SHVEM  CTTGTGGCCTCAGCAGGACAGGCCCCGGGCACTGCCTCACAGCCAAGGCTGGACTGGGTT
           1680      1690      1700      1710      1720      1730

1560      1570      1580      1590      1600      1610
HVEM   GGCTGCAGTGTGGTGTTTAGTGGATACCACATCGGAAGTGATTTTCTAAATTGGATTTGA
       ::::::::::::::::::::::::::::::::::::::::::::::::::::::::::::
SHVEM  GGCTGCAGTGTGGTGTTTAGTGGATACCACATCGGAAGTGATTTTCTAAATTGGATTTGA
           1740      1750      1760      1770      1780      1790

1620      1630      1640      1650      1660      1670
HVEM   ATTCCGGTCCTGTCTTCTATTTGTCATGAAACAGTGTATTTGGGGAGATGCTGTGGGAGG
       ::::  : :::::::  ::::::::::::::::::::::::::::::::::::::::::
SHVEM  ATTCGGCTCCTGTTTTCTATTTGTCATGAAACAGTGTATTTGGGGAGATGCTGTGGGAGG
           1800      1810      1820      1830      1840      1850

1680      1690      1700      1710      1720
HVEM   ATGTAAATATCTTGTTTCTCCTCAAAAAAAAAAAAAAAAAAAAAAAAAA-----------
       :::::::::::::::::::::::::::::::::::::::::::::::::
SHVEM  ATGTAAATATCTTGTTTCTCCTCAAAAAAAAAAAAAAAAAAAAAAAAAAAAAAAAAAAAA
           1860      1870      1880      1890      1900      1910

HVEM   ------------------------------------------------------------

SHVEM  AAAAAAAAAAAA
```

FIG. 2D

```
         10        20        30        40        50        60
HVEM   MEPPGDWGPPPWRSTPRTDVLRLVLYLTFLGAPCYAPALPSCKEDEYPVGSECCPKCSPG
       ::::::::::::::::::::::::::::::::::::::::::::::::::::::::::::
sHVEM  MEPPGDWGPPPWRSTPRTDVLRLVLYLTFLGAPCYAPALPSCKEDEYPVGSECCPKCSPG
         10        20        30        40        50        60

70        80        90       100       110       120
HVEM   YRVKEACGELTGTVCEPCPPGTYIAHLNGLSKCLQCQMCDPAMGLRASRNCSRTENAVCG
       ::::::::::::::::::::::::::::::::::::::::::::::::::::::::::::
sHVEM  YRVKEACGELTGTVCEPCPPGTYIAHLNGLSKCLQCQMCDPAMGLRASRNCSRTENAVCG
         70        80        90       100       110       120

130       140       150       160       170       180
HVEM   CSPGHFCIVQDGDHCAACRAYATSSPGQRVQKGGTESQDTLCQNCPPGTFSPNGTLEECQ
       ::::::::::::::::::::::::::::::::::::::::::::::::::::::::::::
sHVEM  CSPGHFCIVQDGDHCAACRAYATSSPGQRVQKGGTESQDTLCQNCPPGTFSPNGTLEECQ
        130       140       150       160       170       180

190       200       210       220       230       240
HVEM   HQTKCSWLVTKAGAGTSSSHWVWWFLSGSLVIVIVCSTVGLIICVKRRKPRGDVVKVIVS
       :::. .:      .
sHVEM  HQTNRAWKSQTDL*----------------------------------------------
        190

250       260       270       280
HVEM   VQRKRQEAEGEATVIEALQAPPDVTTVAVEETIPSFTGRSPNH*

```
   1  GTCGACCCACGCGTCCGGATGAAGGACCGCAGCAATGGCGCTGAGTTCCTCTGCTGGAGT
  61  TCATCCTGCTAGCTGGGTTCCCGAGCTGCCGGTCTGAGCCTGAGGCATGGAGCCTCCTGG
   1                                                  M  E  P  P  G

121  AGACTGGGGGCCTCCTCCCTGGAGATCCACCCCCAGAACCGACGTCTTGAGGCTGGTGCT
   6   D  W  G  P  P  P  W  R  S  T  P  R  T  D  V  L  R  L  V  L

181  GTATCTCACCTTTCTGGGAGCCCCCTGCTACGCCCCAGCTCTGCCGTCCTGCAAGGAGGA
  26   Y  L  T  F  L  G  A  P  C  Y  A  P  A  L  P  S  C  K  E  D

241  CGAGTACCCAGTGGGCTCCGAGTGCTGCCCCAAGTGCAGTCCAGGTTATCGTGTGAAGGA
  46   E  Y  P  V  G  S  E  C  C  P  K  C  S  P  G  Y  R  V  K  E

301  GGCCTGCGGGGAGCTGACGGGCACAGTGTGTGAACCCTGCCCTCCAGGCACCTACATTGC
  66   A  C  G  E  L  T  G  T  V  C  E  P  C  P  P  G  T  Y  I  A

361  CCACCTCAATGGCCTAAGCAAGTGTCTGCAGTGCCAAATGTGTGACCCAGCCATGGGCCT
  86   H  L  N  G  L  S  K  C  L  Q  C  Q  M  C  D  P  A  M  G  L

421  GCGCGCGAGCCGGAACTGCTCCAGGACAGAGAACGCCGTGTGTGGCTGCAGCCCAGGCCA
 106   R  A  S  R  N  C  S  R  T  E  N  A  V  C  G  C  S  P  G  H

481  CTTCTGCATCGTCCAGGACGGGGACCACTGCGCCGCGTGCCGCGCTTACGCCACCTCCAG
 126   F  C  I  V  Q  D  G  D  H  C  A  A  C  R  A  Y  A  T  S  S

541  CCCGGGCCAGAGGGTGCAGAAGGGAGGCACCGAGAGTCAGGACACCCTGTGTCAGAACTG
 146   P  G  Q  R  V  Q  K  G  G  T  E  S  Q  D  T  L  C  Q  N  C

601  CCCCCCGGGGACCTTCTCTCCCAATGGGACCCTGGAGGAATGTCAGCACCAGACCAATTG
 166   P  P  G  T  F  S  P  N  G  T  L  E  E  C  Q  H  Q  T  N  W

661  GCCTAATCATATGTGTGAAAAGAAGAAAGCCAAGGGGTGAGCACACGGCGGCCCCATCAG
 186   P  N  H  M  C  E  K  K  K  A  K  G  *

721  GGCTCATGTCCCCAGCCGTCACCTCTTGGAGCTCTGTCACCCCAAGCCTGGGAGGTGGCC
 781  CCAGAGCTTTTCCAGGATCCGCGGCTCCTCCCAGGGCAGCCACTGCAGGCTGGGGCAGGT
 841  GATGTAGTCAAGGTGATCGTCTCCATCCAGCGGAAAAGACAGGAGGCAGAAGGTGAGGCC
 901  ACAGTCATTGAGGCCCTGCAGGCCCCTCCGGACGTCACCACGGTGGCCGTGGAGGAGACA
 961  ATACCCTCATTCACGGGGAGGAGCCCAAACCACTGACCCACAGACTCTGCACCCCGACGC
1021  CAGAGATACCTGGAGCGACGGCTGCTGAAAGAGGCTGTCCACCTGGCGAAACCACCGGAG
1081  CCCGGAGGCTTGGGGGCTCCGCCCTGGGCTGGCTTCCGTCTCCTCCAGTGGAGGGAGAGG
1141  TGGGGCCCCTGCTGGGTAGAGCTGGGGACGCCACGTGCCATTCCCATGGGCCAGTGAGG
1201  GCCTGGGGCCTCTGTTCTGCTGTGGCCTGAGCTCCCCAGAGTCCTGAGGAGGAGCGCCAG
1261  TTGCCCCTCGCTCACAGACCACACACCCAGCCCTCCTGGGCCAGCCCAGAGGGCCTTCA
1321  GACCCCAGCTGTCTGCGCGTCTGACTCTTGTGGCCTCAGCAGGACAGGCCCCGGGCACTG
1381  CCTCACAGCCAAGGCTGGACTGGGTTGGCTGCAGTGTGGTGTTTAGTGGATACCACATCG
1441  GAAGTGATTTTCTAAATTGGATTTGAATTCGGCTCCTGTTTTCTATTTGTCATGAAACAG
1501  TGTATTTGGGGAGATGCTGTGGGAGGATGTAAATATCTTGTTTCTCCTCAAAAAAAAAA
1561  AAAAAAAAAAAAAAAAAAAAAAAAAAAAAAAAA
```

FIG. 5

```
            10
sHVEM1  GTCGACCCACGCGTCCG--------------GA-----------------------
        ::::::::::::::::::              ::
sHVEM2  GTCGACCCACGCGTCCGCTCGGCTTTGCCTGGACAGCTCCTGCCTCCCGCAGGGCCCACC
            10        20        30        40        50        60

------------------------------------------------------------
        TGTGTCCCCCAGCGCCGCTCCACCCAGCAGGCCTGAGCCCCTCTCTGCTGCCAGACACCC
            70        80        90       100       110       120

20
        ----------------------------TGAAG-----------------------
                                    :::..:
        CCTGCTGCCCACTCTCCTGCTGCTCGGGTTCTGAGGCACAGCTTGTCACACCGAGGCGGA
           130       140       150       160       170       180

30        40        50
        ----------------------------GACCGCAGCAATGGCGCTGAGTTCCT
                                    ..:::::::::::::::::::::::
        TTCTCTTTCTCTTTCTCTTCTGGCCCACAGCCGCAGCAATGGCGCTGAGTTCCT
           190       200       210       220       230       240

60        70        80        90       100       110
        CTGCTGGAGTTCATCCTGCTAGCTGGGTTCCCGAGCTGCCGGTCTGAGCCTGAGGCATGG
        ::::::::::::::::::::::::::::::::::::::::::::::::::::::::::::
        CTGCTGGAGTTCATCCTGCTAGCTGGGTTCCCGAGCTGCCGGTCTGAGCCTGAGGCATGG
           250       260       270       280       290       300

120       130       140       150       160       170
        AGCCTCCTGGAGACTGGGGGCCTCCTCCCTGGAGATCCACCCCCAGAACCGACGTCTTGA
        ::::::::::::::::::::::::::::::::::::::::::::::::::::::::::::
        AGCCTCCTGGAGACTGGGGGCCTCCTCCCTGGAGATCCACCCCCAGAACCGACGTCTTGA
           310       320       330       340       350       360

180       190       200.      210       220       230
        GGCTGGTGCTGTATCTCACCTTTCTGGGAGCCCCCTGCTACGCCCCAGCTCTGCCGTCCT
        :::::::::::::::::::::::: :::::::::::::::::::::::::::::::::::
        GGCTGGTGCTGTATCTCACCTTCCTGGGAGCCCCCTGCTACGCCCCAGCTCTGCCGTCCT
           370       380       390       400       410       420

240       250       260       270       280       290
        GCAAGGAGGACGAGTACCCAGTGGGCTCCGAGTGCTGCCCCAAGTGCAGTCCAGGTTATC
        ::::::::::::::::::::::::::::::::::::::::::::::::::::::::::::
        GCAAGGAGGACGAGTACCCAGTGGGCTCCGAGTGCTGCCCCAAGTGCAGTCCAGGTTATC
           430       440       450       460       470       480

300       310       320       330       340       350
        GTGTGAAGGAGGCCTGCGGGGAGCTGACGGGCACAGTGTGTGAACCCTGCCCTCCAGGCA
        ::::::::::::::::::::::::::::::::::::::::::::::::::::::::::::
        GTGTGAAGGAGGCCTGCGGGGAGCTGACGGGCACAGTGTGTGAACCCTGCCCTCCAGGCA
           490       500       510       520       530       540

360       370       380       390       400       410
        CCTACATTGCCCACCTCAATGGCCTAAGCAAGTGTCTGCAGTGCCAAATGTGTGACCCAG
        ::::::::::::::::::::::::::::::::::::::::::::::::::::::::::::
        CCTACATTGCCCACCTCAATGGCCTAAGCAAGTGTCTGCAGTGCCAAATGTGTGACCCAG
           550       560       570       580       590       600
```

FIG. 6A

```
              420       430       440       450       460       470
    CCATGGGCCTGCGCGCGAGCCGGAACTGCTCCAGGACAGAGAACGCCGTGTGTGGCTGCA
    :::::::::::::::::::::::::::::::::::::::::::::::::::::::::::
    CCATGGGCCTGCGCGCGAGCCGGAACTGCTCCAGGACAGAGAACGCCGTGTGTGGCTGCA
              610       620       630       640       650       660

480       490       500       510       520       530
    GCCCAGGCCACTTCTGCATCGTCCAGGACGGGGACCACTGCGCCGCGTGCCGCGCTTACG
    :::::::::::::::::::::::::::::::::::::::::::::::::::::::::::
    GCCCAGGCCACTTCTGCATCGTCCAGGACGGGGACCACTGCGCCGCGTGCCGCGCTTACG
              670       680       690       700       710       720

540       550       560       570       580       590
    CCACCTCCAGCCCGGGCCAGAGGGTGCAGAAGGGAGGCACCGAGAGTCAGGACACCCTGT
    :::::::::::::::::::::::::::::::::::::::::::::::::::::::::::
    CCACCTCCAGCCCGGGCCAGAGGGTGCAGAAGGGAGGCACCGAGAGTCAGGACACCCTGT
              730       740       750       760       770       780

600       610       620       630       640       650
    GTCAGAACTGCCCCCCGGGGACCTTCTCTCCCAATGGGACCCTGGAGGAATGTCAGCACC
    :::::::::::::::::::::::::::::::::::::::::::::::::::::::::::
    GTCAGAACTGCCCCCCGGGGACCTTCTCTCCCAATGGGACCCTGGAGGAATGTCAGCACC
              790       800       810       820       830       840

660       670       680       690       700
    AGACCAA------TTGGCCTAATCATA-TGTGTGAAAAGAAGAAAGCCAAGGGGTG--AG
    :::::::      ::::  .:.::: ::.    ..:!..  ::::::::::::: ::  :
    AGACCAACCGAGCTTGGAAAAGTCAGACAGACCTCTGAGGTCTCATCCTGGAGCTGCCAC
              850       860       870       880       890       900

710                720       730              740
    CA-CACGGCGGCCC---------CATCAGGGCTCATGTCCCC---AGCC-----GTCAC
    :: :  :.:: :::         :..::: ::  . : :::    ::::       : .:
    CAGCCCAGCCTCCCTGGGACCTGTCTTCACTGCCTGGGGCCCTGGGAGCCAGGGAGGCTC
              910       920       930       940       950       960

750       .   760       770
    C---------------TCTTGGAGCT----CTGTCAC-CCCAAG-CCTGGG--------
    :                .:: :: :::    :::: :.: ::::  : :::  ::
    CCTGAGGCTGAGTGAACACTGGGCGCTGCACCTGCCTCTCCCACGTCCTCGGCCCCACTC
              970       980       990       1000      1010      1020

780            790       800
    ----AGGTG--GC---C------CCAGAGCTTTTCCAGGATCC-GCGGCTCC--------
    :::::   ::      :         : ...:   . .::::..:.:.::::
    CCGCAGGTGCAGCTGGCTGGTGACGAAGGCCGGAGCTGGGACCAGCAGCTCCCACTGGGT
              1030      1040      1050      1060      1070      1080

810                 820                     830
    -----------TCCCAGGG---------CAGC--------------CACTGCAGGC-----
               :: :::::          :: :                :::.: .:::
    ATGGTGGTTTCTCTCAGGGAGCCTCGTCATCGTCATTGTTTGCTCCACAGTTGGCCTAAT
              1090      1100      1110      1120      1130      1140

840       850       860
    ----TGGG-------------GC----AGGTGATGTAGTCAAGGTGATCGTCTCCATCCA
    :: :                 ::      .:::::::::::::::::::::::::::::
    CATATGTGTGAAAAGAAGAAAGCCAAGGGGTGATGTAGTCAAGGTGATCGTCTCCATCCA
              1150      1160      1170      1180      1190      1200

870       880       890       900       910       920
    GCGGAAAAGACAGGAGGCAGAAGGTGAGGCCACAGTCATTGAGGCCCTGCAGGCCCCTCC
    :::::::::::::::::::::::::::::::::::::::::::::::::::::::::::
    GCGGAAAAGACAGGAGGCAGAAGGTGAGGCCACAGTCATTGAGGCCCTGCAGGCCCCTCC
              1210      1220      1230      1240      1250      1260
```

FIG. 6B

```
 930       940       950       960       970       980
   GGACGTCACCACGGTGGCCGTGGAGGAGACAATACCCTCATTCACGGGGAGGAGCCCAAA
   ::::::::::::::::::::::::::::::::::::::::::::::::::::::::::::
   GGACGTCACCACGGTGGCCGTGGAGGAGACAATACCCTCATTCACGGGGAGGAGCCCAAA
      1270      1280      1290      1300      1310      1320

990       1000      1010      1020      1030      1040
   CCACTGACCCACAGACTCTGCACCCCGACGCCAGAGATACCTGGAGCGACGGCTGCTGAA
   ::::::::::::::::::::::::::::::::::::::::::::::::::::::::::::
   CCACTGACCCACAGACTCTGCACCCCGACGCCAGAGATACCTGGAGCGACGGCTGCTGAA
      1330      1340      1350      1360      1370      1380

1050      1060      1070      1080      1090      1100
   AGAGGCTGTCCACCTGGCGAAACCACCGGAGCCCGGAGGCTTGGGGGCTCCGCCCTGGGC
   ::::::::::::::::::::::::::::::::::::::::::::::::::::::::::::
   AGAGGCTGTCCACCTGGCGAAACCACCGGAGCCCGGAGGCTTGGGGGCTCCGCCCTGGGC
      1390      1400      1410      1420      1430      1440

1110      1120      1130      1140      1150      1160
   TGGCTTCCGTCTCCTCCAGTGGAGGGAGAGGTGGGGCCCCTGCTGGGGTAGAGCTGGGGA
   ::::::::::::::::::::::::::::::::::::::::::::::::::::::::::::
   TGGCTTCCGTCTCCTCCAGTGGAGGGAGAGGTGGGGCCCCTGCTGGGGTAGAGCTGGGGA
      1450      1460      1470      1480      1490      1500

1170      1180      1190      1200      1210      1220
   CGCCACGTGCCATTCCCATGGGCCAGTGAGGGCCTGGGGCCTCTGTTCTGCTGTGGCCTG
   ::::::::::::::::::::::::::::::::::::::::::::::::::::::::::::
   CGCCACGTGCCATTCCCATGGGCCAGTGAGGGCCTGGGGCCTCTGTTCTGCTGTGGCCTG
      1510      1520      1530      1540      1550      1560

1230      1240      1250      1260      1270      1280
   AGCTCCCCAGAGTCCTGAGGAGGAGCGCCAGTTGCCCCTCGCTCACAGACCACACACCCA
   ::::::::::::::::::::::::::::::::::::::::::::::::::::::::::::
   AGCTCCCCAGAGTCCTGAGGAGGAGCGCCAGTTGCCCCTCGCTCACAGACCACACACCCA
      1570      1580      1590      1600      1610      1620

1290      1300      1310      1320      1330      1340
   GCCCTCCTGGGCCAGCCCAGAGGGCCCTTCAGACCCCAGCTGTCTGCGCGTCTGACTCTT
   ::::::::::::::::::::::::::::::::::::::::::::::::::::::::::::
   GCCCTCCTGGGCCAGCCCAGAGGGCCCTTCAGACCCCAGCTGTCTGCGCGTCTGACTCTT
      1630      1640      1650      1660      1670      1680

1350      1360      1370      1380      1390      1400
   GTGGCCTCAGCAGGACAGGCCCCGGGCACTGCCTCACAGCCAAGGCTGGACTGGGTTGGC
   ::::::::::::::::::::::::::::::::::::::::::::::::::::::::::::
   GTGGCCTCAGCAGGACAGGCCCCGGGCACTGCCTCACAGCCAAGGCTGGACTGGGTTGGC
      1690      1700      1710      1720      1730      1740

1410      1420      1430      1440      1450      1460
   TGCAGTGTGGTGTTTAGTGGATACCACATCGGAAGTGATTTTCTAAATTGGATTTGAATT
   ::::::::::::::::::::::::::::::::::::::::::::::::::::::::::::
   TGCAGTGTGGTGTTTAGTGGATACCACATCGGAAGTGATTTTCTAAATTGGATTTGAATT
      1750      1760      1770      1780      1790      1800

1470      1480      1490      1500      1510      1520
   CGGCTCCTGTTTTCTATTTGTCATGAAACAGTGTATTTGGGGAGATGCTGTGGGAGGATG
   ::::::::::::::::::::::::::::::::::::::::::::::::::::::::::::
   CGGCTCCTGTTTTCTATTTGTCATGAAACAGTGTATTTGGGGAGATGCTGTGGGAGGATG
      1810      1820      1830      1840      1850      1860

1530      1540      1550      1560      1570      1580
   TAAATATCTTGTTTCTCCTCAAAAAAAAAAAAAAAAAAAAAAAAAAAAAAAAAAAAAAAA
   ::::::::::::::::::::::::::::::::::::::::::::::::::::::::::::
   TAAATATCTTGTTTCTCCTCAAAAAAAAAAAAAAAAAAAAAAAAAAAAAAAAAAAAAAAA
      1870      1880      1890      1900      1910      1920
```

FIG. 6C

```
1590        1600
    AAAAAAA--GGGCGGCCG-----C----------------------------------
    :::::::  :::::::::     :
    AAAAAAAAAGGGCGGCCGNTAGACTAGTCTAGAGAAAAAACCTCCCACACCTCCCCCTGA
        1930        1940        1950      1960       1970       1980

------------------------------

ACCTGAAACATAAAATGAATGCAATTG
     1990       2000
```

FIG. 6D

```
              10         20         30         40         50         60
sHVEM1  MEPPGDWGPPPWRSTPRTDVLRLVLYLTFLGAPCYAPALPSCKEDEYPVGSECCPKCSPG
        ::::::::::::::::::::::::::::::::::::::::::::::::::::::::::::
sHVEM2  MEPPGDWGPPPWRSTPRTDVLRLVLYLTFLGAPCYAPALPSCKEDEYPVGSECCPKCSPG
              10         20         30         40         50         60

70         80         90        100        110        120
sHVEM1  YRVKEACGELTGTVCEPCPPGTYIAHLNGLSKCLQCQMCDPAMGLRASRNCSRTENAVCG
        ::::::::::::::::::::::::::::::::::::::::::::::::::::::::::::
sHVEM2  YRVKEACGELTGTVCEPCPPGTYIAHLNGLSKCLQCQMCDPAMGLRASRNCSRTENAVCG
              70         80         90        100        110        120

130        140        150        160        170        180
sHVEM1  CSPGHFCIVQDGDHCAACRAYATSSPGQRVQKGGTESQDTLCQNCPPGTFSPNGTLEECQ
        ::::::::::::::::::::::::::::::::::::::::::::::::::::::::::::
sHVEM2  CSPGHFCIVQDGDHCAACRAYATSSPGQRVQKGGTESQDTLCQNCPPGTFSPNGTLEECQ
             130        140        150        160        170        180

190
sHVEM1  HQTNRAW----KSQTDLN
        :::::..    :  ..  :
sHVEM2  HQTNWPNHMCEKKKAKGN
                  190
```

FIG. 7

MOLECULES OF THE HERPESVIRUS-ENTRY-MEDIATOR-RELATED PROTEIN FAMILY AND USES THEREOF

BACKGROUND OF THE INVENTION

Members of the tumor necrosis factor receptor (TNFR) superfamily regulate a diverse range of cellular processes including cell proliferation, programmed cell death and immune responses. Characteristically, these receptors are transmembrane (type 1) glycoproteins having cysteine-rich subdomains in their extracellular, ligand binding domain (Gruss (1996) *Int. J. Clin. Lab. Res.* 26:143–159).

A recently identified member of the TNFR superfamily is the herpesvirus entry mediator (HVEM) (Montgomery et al. (1996) *Cell* 87:427–436). HVEM mediates the entry of many strains of herpes simplex virus (HSV) into cells. Studies have revealed that HSV initiates infection by binding cell surface glycosaminoglycans. To actually enter the cell, the virus requires mediator activity, which is provided by HVEM. HVEM interacts with the virus by binding to the envelope glycoprotein D (gD) and triggering membrane fusion (Whitbeck et al. (1997) *J. Virol.* 71:6083–6093; Montgomery et al., supra).

To date, two ligands of HVEM have been identified, LIGHT and Lymphotoxin α (LTα) (Mauri et al. (1998) Immunity, 8:21–30). LIGHT is a novel cytokine and is termed LIGHT because it shows homology to Lymphotoxins, exhibits Inducible expression and competes with HSV Glycoprotein D for HVEM, a receptor expressed by T lymphocytes. The second identified ligand of HVEM, LTα, is expressed exclusively by T-cells, has 30% sequence identity to TNF, and competes with TNF for binding to the TNF1 receptor. The biological effects exerted by LTα are similar to those of TNF. However, unlike TNF, LTα usually acts as a local paracrine factor. LTα has been shown to be a potent activator of neutrophils. Accordingly, it is thought to be a regulator of acute phase inflammatory reactions. In addition, LTα facilitates leukocyte extravasation by increasing leukocyte adhesion and cytokine production.

Recent evidence suggests that HVEM may also play a role in regulating immune responses. Studies have revealed that HVEM can bind to several TNF receptor-associated factors (TRAFs). TRAFs activate stress activated protein kinase-1/c-Jun N-terminal kinase (JNK/SAPK), as well as the transcription factors, Nuclear Factor-KAPPA B (NF-kB), and transcription factor activator protein-1 (AP-1). These transcription factors in turn control the expression of multiple immune, inflammatory, and acute phase genes (Marsters et al. (1997) *J. Biol. Chem.* 272:14029–14032).

SUMMARY OF THE INVENTION

The present invention is based, at least in part, on the discovery of two cDNA molecules which encode soluble forms of the membrane-bound herpesvirus entry mediator (mHVEM), a member of the TNFR superfamily. The cDNA (SEQ ID NO:1) for the first soluble form, soluble herpesvirus entry mediator-1 (sHVEM1), and the cDNA (SEQ ID NO:17) for the second soluble form, soluble herpesvirus entry mediator-2 (sHVEM2), are described below.

The sHVEM1 cDNA (SEQ ID NO:1) has a 579 nucleotide open reading frame (nucleotides 297–875 of SEQ ID NO:1; SEQ ID NO:3) which encodes a 193 amino acid protein (SEQ ID NO:2). This protein includes a predicted signal sequence of about 38 amino acids (from amino acid 1 to about amino acid 38 of SEQ ID NO:2; SEQ ID NO:5; encoded by nucleotide 297 to 410 of SEQ ID NO:1; SEQ ID NO:6). sHVEM1 has a predicted mature protein length of about 155 amino acids (from about amino acid 39 to amino acid 193 of SEQ ID NO:2; SEQ ID NO:4). sHVEM1 protein possesses three of the four cysteine-rich repeats/domains characteristic of members of the TNFR family. The first cysteine rich domain is 35 amino acids long (amino acid 41 to about amino acid 75 of SEQ ID NO:2; SEQ ID NO:7). The second cysteine rich domain is 44 amino acids long (amino acid 77 to about amino acid 120 of SEQ ID NO:2; SEQ ID NO:8). The third cysteine rich domain is 45 amino acids long (amino acid 121 to about amino acid 165 of SEQ ID NO:2; SEQ ID NO:9). sHVEM1 is predicted to have two potential N-linked glycosylation sites at amino acid 110 of SEQ ID NO:2 and at amino acid 173 of SEQ ID NO:2.

The sHVEM2 cDNA (SEQ ID NO:17) has a 591 nucleotide open reading frame (nucleotides 107–697 of SEQ ID NO:17; SEQ ID NO:19) which encodes a 197 amino acid protein (SEQ ID NO:18). This protein includes a predicted signal sequence of about 38 amino acids (from amino acid 1 to about amino acid 38 of SEQ ID NO:18; SEQ ID NO:21; encoded by nucleotide 107 to 220 of SEQ ID NO:17; SEQ ID NO:22). sHVEM2 has a predicted mature protein length of about 159 amino acids (from about amino acid 39 to amino acid 197 of SEQ ID NO:18; SEQ ID NO:20). sHVEM2 protein possesses three of the four cysteine-rich repeats/domains characteristic of members of the TNFR family. The first cysteine rich domain is 35 amino acids long (amino acid 41 to about amino acid 75 of SEQ ID NO:18; SEQ ID NO:23). The second cysteine rich domain is 44 amino acids long (amino acid 77 to about amino acid 120 of SEQ ID NO:18; SEQ ID NO:24). The third cysteine rich domain is 45 amino acids long (amino acid 121 to about amino acid 165 of SEQ ID NO:18; SEQ ID NO:25). sHVEM2 is predicted to have two potential N-linked glycosylation sites at amino acid 110 of SEQ ID NO:2 and at amino acid 173 of SEQ ID NO:2.

sHVEM2 is 5 amino acids longer than sHVEM1. Overall, sHVEM1 and sHVEM2 share a high degree of sequence identity, exhibiting 76.6% sequence identity at the nucleotide level and 93.9% sequence identity at the amino acid level. The two proteins are identical from amino acid 1 to amino acid 184. It is only at the very C-terminal end of each protein, from amino acid 185 onwards, that their respective sequences differ. sHVEM1 has 9 C-terminal amino acids (amino acid 185–194 of SEQ ID NO:2) that are distinct from the 13 amino acids at the C-terminal end of sHVEM2 (amino acid 185–197 of SEQ ID NO:18).

Nucleotide sequence and amino acid sequence analysis also revealed that the sHVEM1 and sHVEM2 have particularly high sequence identity with membrane-bound herpesvirus entry mediator (mHVEM), a member of the TNF receptor (TNFR) superfamily. For example, sHVEM1 displays 85.1% nucleotide sequence identity and 65% amino acid sequence identity with mHVEM. However, the sHVEM1 and sHVEM2 sequences differ from mHVEM sequence in two important ways. First, sHVEM1 and sHVEM lack the C-terminal end of mHVEM (amino acids 184–283 of SEQ ID NO:13) which contains the transmembrane domain of mHVEM (amino acids 203–225 of SEQ ID NO:13). The absence of a transmembrane domain in sHVEM1 and sHVEM2 suggests that sHVEM1 and sHVEM2 act as soluble receptors. Second, sHVEM1 and sHVEM2 have additional amino acids at their C-terminal ends that are not found at the C-terminal end of mHVEM, e.g., sHVEM1 contains end an additional 10 amino acids at its C-terminal (amino acid 184–193 of SEQ ID NO:2) and sHVEM2 contains an additional 14 amino acids at its C-terminal end (amino acid 184–197). Moreover, these amino acid sequences do not appear to have significant sequence identity with any other known protein.

mHVEM was first identified by its ability to mediate entry of herpes-simplex virus (HSV) into cells (Montogomery et al., supra). Two ligands for mHVEM have been identified, LIGHT (also called TANGO-69, see U.S. Ser. No. 09/146,951, filed Sep. 3, 1998, hereby incorporated by reference) and LTα (Mauri et al., supra). The mechanism by which mHVEM mediates entry of HSV into cells and the role of LIGHT/TANGO-69 and/or LTα in this mechanism is not understood at present. However, it is known that LIGHT/TANGO-69 can compete with HSV for binding to mHVEM (Mauri et al., supra).

As used herein, the term TANGO-69-receptor refers to the sHVEM1 gene, sHVEM2 gene, sHVEM1 and SHVEM2 genes, sHVEM1 protein, sHVEM2 protein, sHVEM1 and sHVEM2 proteins including any and all gene products encoded by the cDNA of SEQ ID NO:1 and SEQ ID NO:17, as described above.

The TANGO-69-receptor is classified as a member of the TNFR superfamily and is predicted to be the soluble form of mHVEM. Soluble forms for most TNFR family members have been described and are thought to arise through proteolytic cleavage (e.g., TNFR p60, TNFR p80, CD27, CD30, CD40 and CD95) or alternative mRNA splicing (e.g., 4-1BB and CD95) (Alderson et al., (1995) *J. Exp Med* 181:71–77; Lantz et al., *J. Clin. Invest.* (1990) 86:1396–1402). The soluble receptor forms of TNFR family members are thought to provide a negative regulatory mechanism by interfering with the activity of the membrane-bound receptor ligand.

The TANGO-69-receptor likely plays a role analogous to other soluble members of the TNFR superfamily by interfering with the ability of LIGHT/TANGO-69 and LTα to bind mHVEM. In addition, TANGO-69-receptor may play a role in HSV entry by modulating the activity of mHVEM. For example, TANGO-69-receptor may bind directly to mHVEM. This interaction can enhance HSV entry or alternatively can inhibit HSV entry by blocking HSV binding to mHVEM. Furthermore, since LIGHT/TANGO-69 is also likely to be a ligand of TANGO-69-receptor, TANGO-69-receptor can modulate the activity of LIGHT/TANGO-69. For example, TANGO-69-receptor can interfere with the binding of LIGHT/TANGO-69 to mHVEM. A consequence of such an interaction can be enhanced HSV entry into cells. Alternatively, TANGO-69-receptor can interact directly with HSV, thereby blocking its ability to bind mHVEM and consequently its ability to infect cells. Thus, the TANGO-69-receptor may be involved in modulating the pathogenesis of HSV.

The activation of a TNFR by a ligand may result in the clustering or crosslinking of different membrane-bound TNF receptors, e.g., TNF-receptor p80, TNF-receptor p60, and TNF-receptor-R, and their ligands TNF, LTα, and LT-β have a complex pattern of cross-binding and can form trimeric/multimeric complexes (Nasismith et al. (1998) TIBS 23:74–79; Armitage et al., (1994) *Curr Opin Immunol* 6:407–13); Gruss et al., (1995) *Cytokines and Molecular Therapy*, 2:75–89). Such crosslinking provides a mechanism by which the functional repertoire of a given ligand can be extended. For example, a ligand can activate distinct signaling pathways and may be involved in regulating cell death, cell survival or cell differentiation. Since LTα is likely to be a ligand for TANGO-69-receptor, TANGO-69-receptor may modulate the activity of LTα. For example, LTα is involved in modulating inflammation and forms hetertrimeric complexes with surface-expressed LT-β, which uses the TNF-receptor type III as a specific receptor (Browning et al. (1993) *Cell,* 73:447–56). The binding of TANGO-69-receptor to LTα may influence its ability to bind LT-β. In turn, the TANGO-69-receptor-LTα complex may activate another signaling pathway such as the apoptotic signaling pathway. LIGHT/TANGO-69 is also thought to be an integral component of the lymphotoxin (LT)/TNF cytokine-receptor system and serves as a membrane-anchored ligand for the LT-β receptor (Mauri et al., supra). The LT/TNF cytokine receptor system is involved in modulating the immune response. Since TANGO-69-receptor is expected to bind LIGHT/TANGO-69, TANGO-69-receptor may be involved in modulating the activity and biological effects of LIGHT/TANGO-69 in the LT/TNF cytokine receptor system.

Moreover, since TANGO-69-receptor is a member of the TNFR superfamily, TANGO-69-receptor may have a function similar to other members of the TNFR superfamily. For example, TNFR family members are involved in programmed cell death, cell proliferation, inflammation and cytotoxicity (Baker et al. (1996) *Oncogene* 12:1–9; Yuan (1997) *Curr Opin Cell Biol* 9:247–251). Recent evidence suggests that mHVEM may be involved in a variety of cellular processes, e.g., mHVEM can associate with members of the TRAF superfamily and activate JNK/SAPK, NF-kB and AP-1 (Marsters et al., supra). JNK/SAPK, NF-kB and AP-1 are known to be mediators of the immune, inflammatory and acute phase response. The ability of TANGO-69-receptor to bind a mHVEM ligand (e.g., LIGHT/TANGO-69 or LTα) or to bind mHVEM may result in an alteration in the mHVEM signaling pathway. Thus, TANGO-69-receptor may modulate the biological activities exerted by mHVEM and accordingly may be involved in modulating disorders such inflammatory bowel disease, sepsis, AIDS or rheumatoid arthritis.

Northern blot analysis revealed that the TANGO-69-receptor is expressed in both stimulated and unstimulated mast cells (see Example 2). This expression pattern suggests that the TANGO-69-receptor may be involved in modulating the activity of mast cells. For example, TANGO-69-receptor may modulate the ability of mast cells to influence T cell function (Pater-Huijsen et al. (1997) *Immunology Letters* 57:47–51). Mast cells play a pathological role in several disease processes, including: delayed hypersensitivity, dermatitis, parasitic infections, asthma, inflammatory rheumatoid arthritis, fibrosis, and inflammatory bowel disease. Accordingly, TANGO-69-receptor may be involved in modulating these disease processes, and modulators of TANGO-69-receptor expression or activity may be useful in treating these disorders.

Northern blot analysis also revealed that the TANGO-69-receptor is expressed in TNF-stimulated endothelial cells. Moreover, the TANGO-69-receptor ligand, LIGHT/TANGO-69, may be involved in regulating the inflammatory response in endothelial cells. For example, LIGHT/TANGO-69 has the ability to modulate the secretion of chemokines from endothelial cells and has the ability to upregulate the expression of adhesion molecules, E-selectin and VCAM. LIGHT/TANGO-69 also has the ability to modulate the binding of platelets to the endothelium and may play a role in regulating coagulation. Thus, TANGO-69-receptor may play an anti-inflammatory role in the endothelium. For example, the binding of TANGO-69-receptor to LIGHT/TANGO-69 may modulate endothelial inflammation. Moreover, TANGO-69-receptor may play a role in regulating endothelial pathogenesis such as vascular infarctions, atherosclerotic lesions and angiogenesis.

Similar to other TNFR family members, the TANGO-69-receptor has cysteine-rich repeats in its C-terminal end. These repeats are expected to play a role in ligand binding. As discussed above, ligands of mHVEM are also expected to function as ligands of TANGO-69-receptor. However, the TANGO-69-receptor differs from mHVEM by containing an extra 10 amino acids at its C-terminal end. Thus, the TANGO-69-receptor may have the ability to bind ligands that do not bind to mHVEM, suggesting that TANGO-69-receptor may possess activities that are not possessed by mHVEM.

Accordingly, in one aspect, the invention provides isolated nucleic acid molecules encoding TANGO-69-receptor proteins or biologically active portions thereof, as well as nucleic acid fragments suitable as primers or hybridization probes for the detection of TANGO-69-receptor-encoding nucleic acids.

The invention features a nucleic acid molecule which is at least 85.5%, 87.5%, 90%, 92.5%, 95%, 97.5%, 98%, 98.5%, or 99% identical to the nucleotide sequence shown in SEQ ID NO:1, SEQ ID NO:3, SEQ ID NO:6, SEQ ID NO:17, SEQ ID NO:19, SEQ ID NO:22, the nucleotide sequence of the cDNA insert of the plasmid deposited with ATCC as Accession Number 98821 (sHVEM1; the "cDNA of ATCC Ephdc4C10"), or a complement thereof. Preferably, the nucleic acid molecule encodes a soluble protein that lacks a transmembrane domain and lacks a cytoplasmic domain.

The invention features a nucleic acid molecule which includes a fragment of at least 300 (325, 350, 375, 400, 425, 450, 500, 550, 600, 650, 700, 800, 900, 1000, or 1300, 1600, or 1929) nucleotides of the nucleotide sequence shown in SEQ ID NO:1, SEQ ID NO:3, SEQ ID NO:6, SEQ ID NO:17, SEQ ID NO:19, SEQ ID NO:22, the nucleotide sequence of the cDNA ATCC 98821, or a complement thereof.

The invention also features a nucleic acid molecule which includes a nucleotide sequence encoding a protein having an amino acid sequence that is at least 66%, 70%, 75%, 80%, 85%, 90%, 95%, 97.5%, 98%, 98.5%, or 99% identical to the amino acid sequence of SEQ ID NO:2, SEQ ID NO:4, SEQ ID NO:5.

In a preferred embodiment, a TANGO-69-receptor nucleic acid molecule has the nucleotide sequence shown SEQ ID NO:1, SEQ ID NO:3, SEQ ID NO:6, SEQ ID NO:17, SEQ ID NO:19, SEQ ID NO:22, the nucleotide sequence of the cDNA of ATCC 98821.

Also within the invention is a nucleic acid molecule which encodes a fragment of a polypeptide having the amino acid sequence of SEQ ID NO:2, SEQ ID NO:4, or SEQ ID NO:5, SEQ ID NO:18, SEQ ID NO:20, SEQ ID NO:21, the fragment including at least 15 (25, 30, 50, 100, 150, or 193) contiguous amino acids of SEQ ID NO:2, SEQ ID NO:4, SEQ ID NO:5, SEQ ID NO:18, SEQ ID NO:20, SEQ ID NO:21, the polypeptide encoded by the cDNA of ATCC Accession Number 98821.

The invention includes a nucleic acid molecule which encodes a naturally occurring allelic variant of a polypeptide comprising the amino acid sequence of SEQ ID NO:2, SEQ ID NO:4, SEQ ID NO:5, or an amino acid sequence encoded by the cDNA of ATCC Accession Number 98821, wherein the nucleic acid molecule hybridizes to a nucleic acid molecule comprising SEQ ID NO:1, SEQ ID NO:3, SEQ ID NO:6, or a complement thereof under stringent conditions.

The invention includes a nucleic acid molecule which encodes a naturally occurring allelic variant of a polypeptide comprising the amino acid sequence of SEQ ID NO:18, SEQ ID NO:20, SEQ ID NO:21, wherein the nucleic acid molecule hybridizes to a nucleic acid molecule comprising SEQ ID NO:17, SEQ ID NO:19, SEQ ID NO:22, or a complement thereof under stringent conditions.

Also within the invention are: an isolated TANGO-69-receptor protein having an amino acid sequence that is at least about 65%, 70, 75%, 80%, 85%, 85%, 87.5%, 90%, 92.5%, 95%, 97.5%, 98%, 98.5%, or 99% identical to the amino acid sequence of SEQ ID NO:4 or SEQ ID NO:20 (mature human TANGO-69-receptor), the amino acid sequence of SEQ ID NO:2 or SEQ ID NO:18 (immature human TANGO-69-receptor) or the amino acid sequence of SEQ ID NO:5 or SEQ ID NO:21 (signal sequence of human TANGO-69-receptor); an isolated TANGO-69-receptor protein having an amino acid sequence that is at least about 66%, 70%, 80%, 85%, 90%, 95%, 97.5%, 98%, 98.5%, or 99% identical to the first cysteine-rich domain of SEQ ID NO:2 (e.g., about amino acid residues 41 to 75 of SEQ ID NO:2; SEQ ID NO:7; an isolated TANGO-69-receptor protein having an amino acid sequence that is at least about 66%, 70%, 75%, 80%, 85%, 90%, 95%, 97.5%, 98%, 98.5% or 99% identical to the second cysteine-rich domain of SEQ ID NO:2 (e.g., about amino acid residues 77 to 120 of SEQ ID NO:2; SEQ ID NO:8); and an isolated TANGO-69-receptor protein having an amino acid sequence that is at least about 66%, 70%, 75%, 80%, 85%, 90%, 95%, 97.5%, 98%, 98.5% or 99% identical to the third cysteine-rich domain of SEQ ID NO:2 (e.g., about amino acid residues 121 to 165 of SEQ ID NO:2; SEQ ID NO:9); an isolated TANGO-69-receptor protein having an amino acid sequence that is at least about 66%, 70%, 75%, 80%, 85%, 90%, 95%, 97.5%, 98%, 98.5%, or 99% identical to the first cysteine-rich domain of SEQ ID NO:18 (e.g., about amino acid residues 41 to 75 of SEQ ID NO:18; SEQ ID NO:23; an isolated TANGO-69-receptor protein having an amino acid sequence that is at least about 66%, 70%, 75%, 80%, 85%, 90%, 95%, 97.5%, 98%, 98.5% or 99% identical to the second cysteine-rich domain of SEQ ID NO:18 (e.g., about amino acid residues 77 to 120 of SEQ ID NO:18; SEQ ID NO:24); and an isolated TANGO-69-receptor protein having an amino acid sequence that is at least about 66%, 70%, 75%, 80%, 85%, 90%, 95%, 95%, 97.5%, 98%, 98.5% or 99% identical to the third cysteine-rich domain of SEQ ID NO:18 (e.g., about amino acid residues 121 to 165 of SEQ ID NO:18; SEQ ID NO:25).

Also within the invention are: an isolated TANGO-69-receptor protein which is encoded by a nucleic acid molecule having a nucleotide sequence that is at least about 85.5%, 87.5%, 90%, 92.5%, 95%, 97.5%, 98%, 98.5%, or 99% identical to SEQ ID NO:3 or SEQ ID NO:19; an isolated TANGO-69-receptor protein which is encoded by a nucleic acid molecule having a nucleotide sequence that is at least about 85.5%, 87%, 90%, 92.5%, 95%, 97.5%, 98%, 98.5%, or 99% identical to SEQ ID NO:6 or SEQ ID NO:22; an isolated TANGO-69-receptor protein which is encoded by a nucleic acid molecule having a nucleotide sequence at least about 85.5%, 87%, 90%, 92.5%, 95%, 97.5%, 98%, 98.5%, or 99% identical to the first cysteine-rich domain encoding portion of SEQ ID NO:1 (e.g., about nucleotides 397 to 521 of SEQ ID NO:1; SEQ ID NO:10); an isolated TANGO-69-receptor protein sequence at least about 66%, 70%, 75%, 80%, 85%, 90%, 95%, 97.5%, 98%, 98.5%, or 99% identical to the second cysteine-rich domain encoding portion of SEQ ID NO:1 (e.g., about nucleotides 526 to 657 of SEQ ID NO:1; SEQ ID NO:11); an isolated TANGO-69-receptor protein which is encoded by a nucleic acid molecule having a nucleotide sequence at least about 85.5%, 90%, 95%, 97.5%, 98%, 98.5%, or 99% identical to the third cysteine-rich domain encoding portion of SEQ ID NO:1 (e.g., about nucleotides 657 to 791 of SEQ ID NO:1; SEQ ID NO:12); an isolated TANGO-69-receptor protein which is encoded by a nucleic acid molecule having a nucleotide sequence at least about 85.5%, 90%, 95%, 97.5%, 98%, 98.5%, or 99% identical to the first cysteine-rich domain encoding portion of SEQ ID NO:17 (e.g., about nucleotides 227 to 331 of SEQ ID NO:17; SEQ ID NO:26); an isolated TANGO-69-receptor protein sequence at least about 66%, 70%, 75%, 80%, 85%, 90%, 95%, 97.5%, 98%, 98.5%, or 99% identical to the second cysteine-rich domain encoding portion of SEQ ID NO:17 (e.g., about nucleotides 335 to 467 of SEQ ID NO:17; SEQ ID NO:27); an isolated TANGO-69-receptor protein which is encoded by a nucleic acid molecule having a nucleotide sequence at least about 85.5%, 90%, 95%, 97.5%, 98%, 98.5%, or 99% identical to the third cysteine-rich domain encoding portion of SEQ ID NO:17 (e.g., about nucleotides 468 to 601 of SEQ ID NO:17; SEQ ID NO:28); and an isolated TANGO-69-receptor protein which is encoded by a nucleic acid molecule having a nucleotide sequence which hybridizes under stringent hybridization conditions to a nucleic acid molecule having the nucleotide sequence of SEQ ID NO:3 or SEQ ID NO:19, their complement, the non-coding strand of the cDNA of ATCC 98821.

Also within the invention is a polypeptide which is a naturally occurring allelic variant of a polypeptide that includes the amino acid sequence of SEQ ID NO:2, SEQ ID NO:4, SEQ ID NO:5, or the cDNA of ATCC 98821, wherein the polypeptide is encoded by a nucleic acid molecule which hybridizes to a nucleic acid molecule comprising SEQ ID NO:1, SEQ ID NO:3, SEQ ID NO:6 or a complement thereof under stringent conditions.

Also within the invention is a polypeptide which is a naturally occurring allelic variant of a polypeptide that includes the amino acid sequence of SEQ ID NO:18, SEQ ID NO:20, SEQ ID NO:21, wherein the polypeptide is encoded by a nucleic acid molecule which hybridizes to a nucleic acid molecule comprising SEQ ID NO:17, SEQ ID NO:19, SEQ ID NO:22, or a complement thereof under stringent conditions.

Another embodiment of the invention features TANGO-69-receptor nucleic acid molecules which specifically detect TANGO-69-receptor nucleic acid molecules relative to nucleic acid molecules encoding other members of the TNF receptor superfamily. For example, in one embodiment, a TANGO-69-receptor nucleic acid molecule hybridizes under stringent conditions to a nucleic acid molecule comprising the nucleotide sequence of SEQ ID NO:1, SEQ ID NO:3, SEQ ID NO:6, SEQ ID NO:17, SEQ ID NO:19, SEQ ID NO:22, the cDNA of ATCC 98821, or a complement thereof. In another embodiment, the TANGO-69-receptor nucleic acid molecule is at least 300 (325, 350, 375, 400, 425, 450, 500, 550, 600, 650, 700, 800, 900, 1000, 1200, 1400, 1600, or 1940) nucleotides in length and hybridizes under stringent conditions to a nucleic acid molecule comprising the nucleotide sequence shown in SEQ ID NO:1, SEQ ID NO:3, SEQ ID NO:6, SEQ ID NO:17, SEQ ID NO:19, SEQ ID NO:22, cDNA of ATCC 98821, or a complement thereof. In a preferred embodiment, an isolated TANGO-69-receptor nucleic acid molecule comprises nucleotides 397 to 521 of SEQ ID NO:1 (SEQ ID NO:9); nucleotides 525 to 696 of SEQ ID NO:1 (SEQ ID NO:10); nucleotides 697 to 791 of SEQ ID NO:1 (SEQ ID NO:11); nucleotides 227 to 331 of SEQ ID NO:17 (SEQ ID NO:26); nucleotides 335 to 467 of SEQ ID NO:17 (SEQ ID NO:27); nucleotides 468 to 601 of SEQ ID NO:17 (SEQ ID NO:28) encoding the cysteine rich domains of TANGO-69-receptor, or a complement thereof. In another embodiment, the invention provides an isolated nucleic acid molecule which is antisense to the coding strand of a TANGO-69-receptor nucleic acid.

Another aspect of the invention provides a vector, e.g., a recombinant expression vector, comprising a TANGO-69-receptor nucleic acid molecule of the invention. In another embodiment the invention provides a host cell containing such a vector. The invention also provides a method for producing TANGO-69-receptor protein by culturing, in a suitable medium, a host cell of the invention containing a recombinant expression vector such that a TANGO-69-receptor protein is produced.

Another aspect of this invention features isolated or recombinant TANGO-69-receptor proteins and polypeptides. Preferred TANGO-69-receptor proteins and polypeptides possess at least one biological activity possessed by naturally occurring human TANGO-69-receptor, e.g., (1) the ability to form protein:protein interactions with proteins in the TANGO-69-receptor signalling pathway; (2) the ability to bind a TANGO-69-receptor ligand, e.g., the ability to bind LIGHT/TANGO-69 or LTα; and (3) the ability to interact with mHVEM. Other activities include: (1) the ability to modulate cellular proliferation (e.g., proliferation of cells of the immune system and endothelial cells); (2) the ability to modulate cellular differentiation (e.g., differentiation of cells of the immune system and endothelial cells); (3) the ability to modulate inflammation (e.g., systemic inflammation or local inflammation); (4) the ability to modulate mast cell activity (e.g., the ability to modulate hypersensitivity); (5) the ability to modulate HSV proliferation (e.g., the ability to modulate the entry of HSV to cells); (6) the ability to modulate cell-cell interaction (e.g., the ability to modulate cell adhesion); and (7) the ability to modulate coagulation (e.g., the ability to modulate the binding of platelets to the endothelium).

The TANGO-69-receptor proteins of the present invention, or biologically active portions thereof, can be operably linked to a non-TANGO-69-receptor polypeptide (e.g., heterologous amino acid sequences) to form TANGO-69-receptor fusion proteins. The invention further features antibodies that specifically bind TANGO-69-receptor proteins, such as monoclonal or polyclonal antibodies. In addition, the TANGO-69-receptor proteins or biologically active portions thereof can be incorporated into pharmaceutical compositions, which optionally include pharmaceutically acceptable carriers.

In another aspect, the present invention provides a method for detecting the presence of TANGO-69-receptor activity or expression in a biological sample by contacting the biological sample with an agent capable of detecting an indicator of TANGO-69-receptor activity such that the presence of TANGO-69-receptor activity is detected in the biological sample.

In another aspect, the invention provides a method for modulating TANGO-69-receptor activity comprising contacting a cell with an agent that modulates (inhibits or stimulates) TANGO-69-receptor activity or expression such that TANGO-69-receptor activity or expression in the cell is modulated. In one embodiment, the agent is an antibody that specifically binds to TANGO-69-receptor protein. In another embodiment, the agent modulates expression of TANGO-69-receptor by modulating transcription of a TANGO-69- receptor gene, splicing of a TANGO-69-receptor mRNA, or translation of a TANGO-69-receptor mRNA. In yet another embodiment, the agent is a nucleic acid molecule having a nucleotide sequence that is antisense to the coding strand of the TANGO-69-receptor mRNA or the TANGO-69-receptor gene.

In one embodiment, the methods of the present invention are used to treat a subject having a disorder characterized by aberrant TANGO-69-receptor protein activity or nucleic acid expression by administering an agent which is a TANGO-69-receptor modulator to the subject. In one embodiment, the TANGO-69-receptor modulator is a TANGO-69-receptor protein. In another embodiment, the TANGO-69-receptor modulator is a TANGO-69-receptor nucleic acid molecule. In other embodiments, the TANGO-69-receptor modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a TANGO-69-receptor protein; (ii) mis-regulation of a gene encoding a TANGO-69-receptor protein; and (iii) aberrant post-translational modification of a TANGO-69-receptor protein, wherein a wild-type form of the gene encodes a protein with a TANGO-69-receptor activity.

In another aspect, the invention provides a method for identifying a compound that binds to or modulates the activity of a TANGO-69-receptor protein. In general, such methods entail measuring a biological activity of a TANGO-69-receptor protein in the presence and absence of a test compound and identifying those compounds which alter the activity of the TANGO-69-receptor protein.

The invention also features methods for identifying a compound which modulates the expression of TANGO-69-receptor by measuring the expression of TANGO-69-receptor in the presence and absence of a compound.

Other features and advantages of the invention will be apparent from the following detailed description and claims.

BRIEF DESCRIPTION OF THE DRAWINGS

FIG. 1 depicts the cDNA sequence (SEQ ID NO:1) and predicted amino acid sequence (SEQ ID NO:2) of human soluble Herpesvirus Entry Mediator-1 (sHVEM1) (also referred to as "TANGO-69-receptor"). The open reading frame of SEQ ID NO:1 extends from nucleotide 297 to nucleotide 875 (SEQ ID NO:3).

FIGS. 2A–2D depicts an alignment of the nucleotide sequence of sHVEM1 (SEQ ID NO:1) and membrane-bound form of Herpesvirus Entry Mediator (mHVEM) (SEQ ID NO:14).

FIG. 3 depicts an alignment of the amino acid sequence of sHVEM1 (SEQ ID NO:2) and mHVEM (SEQ ID NO:13).

FIG. 5 depicts the cDNA sequence (SEQ ID NO:17) and predicted amino acid sequence (SEQ ID NO:18) of human soluble Herpesvirus Entry Mediator-2 (sHVEM2) (also referred to as "TANGO-69-receptor"). The open reading frame of SEQ ID NO:17 extends from nucleotide 107 to nucleotide 697 (SEQ ID NO:19).

FIGS. 6A–6D depicts an alignment of the nucleotide sequence of sHVEM1 (SEQ ID NO:1) and sHVEM2 (SEQ ID NO:17).

FIG. 7 depicts an alignment of the amino acid sequence of sHVEM1 (SEQ ID NO:2) and sHVEM2 (SEQ ID NO:18).

DETAILED DESCRIPTION OF THE INVENTION

Figure 4:
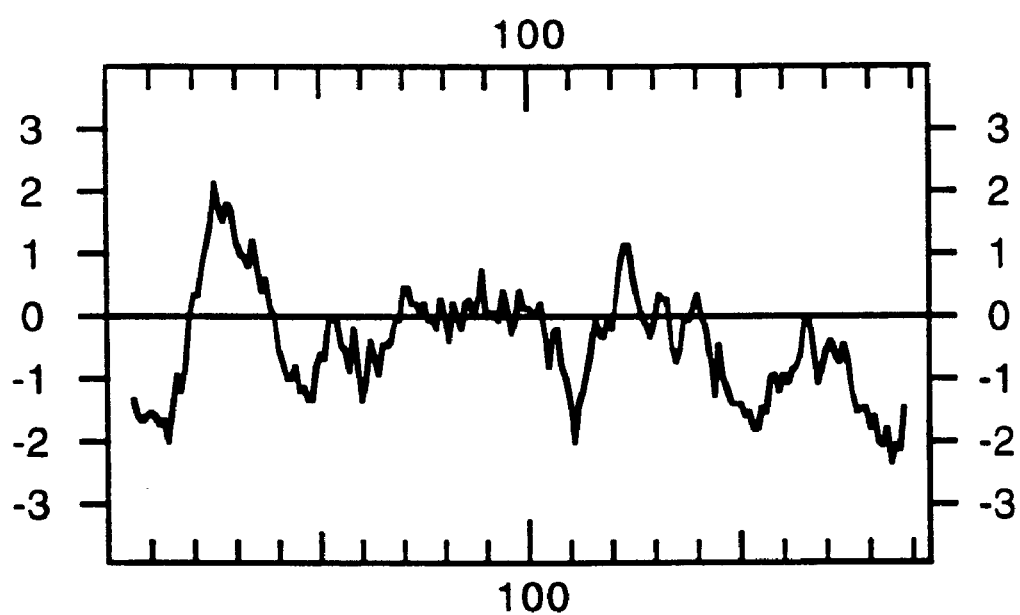
FIG. 4 is a hydropathy plot of sHVEM1.

The present invention is based on the discovery of two cDNA molecules which encode soluble forms of the membrane-bound herpesvirus entry mediator (mHVEM), and are predicted to be members of the TNF receptor superfamily. The cDNA for first soluble herpesvirus entry mediator-1 (sHVEM1) and the cDNA for second soluble herpesvirus entry mediator-2 (sHVEM2) are described below.

A nucleotide sequence encoding sHVEM1 is shown in FIG. 1 (SEQ ID NO:1; SEQ ID NO:3 includes the open reading frame only). A predicted amino acid sequence of sHVEM1 protein is also shown in FIG. 1 (SEQ ID NO:2).

A nucleotide sequence encoding sHVEM2 is shown in FIG. 5 (SEQ ID NO:17; SEQ ID NO:19 includes the open reading frame only). A predicted amino acid sequence of sHVEM2 protein is also shown in FIG. 5 (SEQ ID NO:18).

The sHVEM cDNA of FIG. 1 (SEQ ID NO:1), which is approximately 1929 nucleotides long including untranslated regions, encodes a protein amino acid having a molecular weight of approximately 20.76 kDa (excluding post-translational modifications). A plasmid containing a cDNA encoding human sHVEM1 (with the cDNA insert name of Ephdc4c10) was deposited with American Type Culture Collection (ATCC), Manassas, Va. on Jul. 17, 1998 and assigned Accession Number 98821. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

The sHVEM2 cDNA of FIG. 5 (SEQ ID NO:17), which is approximately 1596 nucleotides long including untranslated regions, encodes a protein amino acid having a molecular weight of approximately 21.22 kDa (excluding post-translational modifications). A plasmid containing a cDNA encoding human sHVEM2 was deposited with American Type Culture Collection (ATCC), Manassas, Va. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

sHVEM1 and sHVEM2 share a high degree of sequence identity exhibiting 76.6% sequence identity at the nucleotide level and 93.9% sequence identity at the amino acid level. The two proteins are identical from amino acid 1 to amino acid 184. It is only at the very C-terminal of each protein, from amino acid 185 onwards, that their respective sequences differ, i.e., sHVEM1 has 9 C-terminal amino acids (amino acid 185–193 of SEQ ID NO:2) that are distinct from the 13 amino acids at the C-terminal end of sHVEM2 (amino acid 185–197).

Nucleotide sequence and amino acid sequence analysis also revealed that the sHVEM1 and sHVEM2 have particularly high sequence identity with membrane-bound herpesvirus entry mediator (mHVEM), a member of the TNF receptor (TNFR) superfamily. For example, sHVEM1 displays 85.1% nucleotide sequence identity and 65% amino acid sequence identity with mHVEM. However, the sHVEM1 and sHVEM2 sequences differ from mHVEM sequence in two main ways. First, sHVEM1 and sHVEM lack the C-terminal end of mHVEM (amino acids 184–283 of SEQ ID NO:13) which contains the transmembrane domain of mHVEM (amino acids 203–225 of SEQ ID NO:13). The absence of a transmembrane domain in the sHVEM1 and sHVEM2 suggests that sHVEM1 and sHVEM2 act as soluble receptors. Secondly, sHVEM1 and sHVEM2 have additional amino acids at their C-terminal ends that are not found at the C-terminal end of mHVEM, e.g., sHVEM1 contains an additional 10 amino acids at its C-terminal end (amino acid 184–193 of SEQ ID NO:2) and sHVEM2 contains an additional 14 amino acids at its C-terminal end (amino acid 184–197). Moreover, these amino acid sequences do not appear to have significant sequence identity with any other known protein.

As used herein, the term TANGO-69-receptor refers to the sHVEM1 gene, sHVEM2 gene, sHVEM1 and SHVEM2 genes, sHVEM1 protein, sHVEM2 protein, sHVEM1 and sHVEM2 proteins including any and all gene products encoded by the CDNA of SEQ ID NO:1 and SEQ ID NO:17, as described above.

Northern blot analysis revealed that an approximate 2 kb sHVEM1 mRNA transcript is present at similar levels in stimulated and unstimulated mast cells. Northern blot analysis also revealed the presence of a 2 kb sHVEM1 mRNA in stimulated human umbilical vein endothelial cells (HUVECs). No sHVEM1 mRNA was observed in unstimulated HUVECs. The expression pattern of sHVEM1 suggests that sHVEM1 may play a role in allergic reactions and may play an anti-inflammatory role in the endothelium.

Human TANGO-69-receptor are members of a family of molecules (the "TANGO-69-receptor family") having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

In one embodiment, a TANGO-69-receptor protein includes a cysteine rich domain having at least 66%, 70%, 75%, 80%, 85%, 87%, 90%, 92.5%, 95%, 97.5%, 98%, 98.5%, or 99% amino acid sequence identity to the cysteine rich domain of other TNFR cysteine rich domains.

Preferred TANGO-69-receptor polypeptides of the present invention have an amino acid sequence sufficiently identical to the cysteine-rich domains of SEQ ID NO:7, SEQ ID NO:8, SEQ ID NO:9, SEQ ID NO:23, SEQ ID NO:24, AND SEQ ID NO:25. As used herein, the term "sufficiently identical" refers to a first amino acid or nucleotide sequence which contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 85% identity, preferably 90% identity, more preferably 95%, 97.5% or 98% identity are defined herein as sufficiently identical.

As used interchangeably herein a "TANGO-69-receptor activity", "biological activity of TANGO-69-receptor" or "functional activity of TANGO-69-receptor", refers to an activity exerted by a TANGO-69-receptor protein, polypeptide or nucleic acid molecule on a TANGO-69-receptor responsive cell as determined in vivo, or in vitro, according to standard techniques. A TANGO-69-receptor activity can be a direct activity, such as an association with or an enzymatic activity on a second protein or an indirect activity, such as a cellular signaling activity mediated by interaction of the TANGO-69-receptor protein with a second protein. In a preferred embodiment, a TANGO-69-receptor activity includes at least one or more of the following activities described herein.

Accordingly, another embodiment of the invention features isolated TANGO-69-receptor proteins and polypeptides having a TANGO-69-receptor activity.

Yet another embodiment of the invention features TANGO-69-receptor molecules which contain a signal sequence. Generally, a signal sequence (or signal peptide) is a peptide containing approximately 38 amino acids which occurs at the extreme N-terminal end of secretory and integral membrane proteins and which contains large numbers of hydrophobic amino acid residues and serves to direct a protein containing such a sequence to a lipid bilayer.

Various aspects of the invention are described in further detail in the following subsections.

I. Isolated Nucleic Acid Molecules

One aspect of the invention pertains to isolated nucleic acid molecules that encode TANGO-69-receptor proteins or biologically active portions thereof, as well as nucleic acid molecules sufficient for use as hybridization probes to identify TANGO-69-receptor-encoding nucleic acids (e.g., TANGO-69-receptor mRNA) and fragments for use as PCR primers for the amplification or mutation of TANGO-69-receptor nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated TANGO-69-receptor nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:6, SEQ ID NO:17, SEQ ID NO:19, SEQ ID NO:22, the cDNA of ATCC 98812, or a complement of any of these nucleotide sequences, can be isolated using standard molecular biology techniques and the sequence information provided herein. Using all or a portion of the nucleic acid sequences of SEQ ID NO:1, SEQ ID NO:3, SEQ ID NO:6, SEQ ID NO:17, SEQ ID NO:19, SEQ ID NO:22, the cDNA of ATCC 98821 as a hybridization probe, TANGO-69-receptor nucleic acid molecules can be isolated using standard hybridization and cloning techniques (e.g., as described in Sambrook et al., eds., *Molecular Cloning: A Laboratory Manual*, 2nd ed., *Cold Spring Harbor Laboratory*, Cold Spring Harbor Laboratory Press, Cold Spring Harbor, N.Y., 1989).

A nucleic acid of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to TANGO-69-receptor nucleotide sequences can be prepared by standard synthetic techniques, e.g., using an automated DNA synthesizer.

In another preferred embodiment, an isolated nucleic acid molecule of the invention comprises a nucleic acid molecule which is a complement of the nucleotide sequence shown in SEQ ID NO:1, SEQ ID NO:3, SEQ ID NO:6, SEQ ID NO:17, SEQ ID NO:19, SEQ ID NO:22, the cDNA of ATCC 98821, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding TANGO-69-receptor, for example, a fragment which can be used as a probe or primer or a fragment encoding a biologically active portion of TANGO-69-receptor. The nucleotide sequence determined from the cloning of the human TANGO-69-receptor gene allows for the generation of probes and primers designed for use in identifying and/or cloning TANGO-69-receptor homologues in other cell types, e.g., from other tissues, as well as TANGO-69-receptor homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:3; SEQ ID NO:17, SEQ ID NO:19, the cDNA of ATCC 98821, or of a naturally occurring mutant of SEQ ID NO:1, SEQ ID NO:3, SEQ ID NO:17, SEQ ID NO:19, the cDNA of ATCC 98821.

Probes based on the human TANGO-69-receptor nucleotide sequence can be used to detect transcripts or genomic sequences encoding the same or identical proteins. The probe comprises a label group attached thereto, e.g., a radioisotope, a fluorescent compound, an enzyme, or an enzyme co-factor. Such probes can be used as part of a diagnostic test kit for identifying cells or tissues which mis-express a TANGO-69-receptor protein, such as by measuring levels of a TANGO-69-receptor-encoding nucleic acid in a sample of cells from a subject, e.g., detecting TANGO-69-receptor mRNA levels or determining whether a genomic TANGO-69-receptor gene has been mutated or deleted.

A nucleic acid fragment encoding a "biologically active portion of TANGO-69-receptor" can be prepared by isolating a portion of SEQ ID NO:1, SEQ ID NO:3, SEQ ID NO:17, SEQ ID NO:19, the cDNA of ATCC 98821, which encodes a polypeptide having a TANGO-69-receptor biological activity, expressing the encoded portion of TANGO-69-receptor protein (e.g., by recombinant expression in vitro) and assessing the activity of the encoded portion of TANGO-69-receptor. For example, a nucleic acid fragment encoding a biologically active portion of TANGO-69-receptor includes a cysteine-rich domain, e.g., SEQ ID NO:7, SEQ ID NO:8, SEQ ID NO:9, SEQ ID NO:23, SEQ ID NO:24, and SEQ ID NO:25.

The invention further encompasses nucleic acid molecules that differ from the nucleotide sequence of SEQ ID NO:1, SEQ ID NO:3, SEQ ID NO:17, SEQ ID NO:19, the cDNA of ATCC 98821, due to degeneracy of the genetic code and thus encode the same TANGO-69-receptor protein as that encoded by the nucleotide sequence shown in SEQ ID NO:1, SEQ ID NO:3, SEQ ID NO:17, SEQ ID NO:19, the cDNA of ATCC 98821.

In addition to the human TANGO-69-receptor nucleotide sequence shown in SEQ ID NO:1, SEQ ID NO:3, SEQ ID NO:17, SEQ ID NO:19, the cDNA of ATCC 98821, it will be appreciated by those skilled in the art that DNA sequence polymorphisms that lead to changes in the amino acid sequences of TANGO-69-receptor may exist within a population (e.g., the human population). Such genetic polymorphism in the TANGO-69-receptor gene may exist among individuals within a population due to natural allelic variation. An allele is one of a group of genes which occur alternatively at a given genetic locus. As used herein, the phrase "allelic variant" refers to a nucleotide sequence which occurs at a TANGO-69-receptor locus or to a polypeptide encoded by the nucleotide sequence. As used herein, the terms "gene" and "recombinant gene" refer to nucleic acid molecules comprising an open reading frame encoding a TANGO-69-receptor protein, preferably a mammalian TANGO-69-receptor protein. Such natural allelic variations can typically result in 1–5% variance in the nucleotide sequence of the TANGO-69-receptor gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations in TANGO-69-receptor that are the result of natural allelic variation and that do not alter the functional activity of TANGO-69-receptor are intended to be within the scope of the invention.

Moreover, nucleic acid molecules encoding TANGO-69-receptor proteins from other species (TANGO-69-receptor homologues), which have a nucleotide sequence which differs from that of a human TANGO-69-receptor, are intended to be within the scope of the invention. Nucleic acid molecules corresponding to natural allelic variants and homologues of the TANGO-69-receptor cDNA of the invention can be isolated based on their identity to the human TANGO-69-receptor nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 300 (325, 350, 375, 400, 425, 450, 500, 550, 600, 650, 700, 800, 900, 1000, or 1290) nucleotides in length and hybridizes under stringent conditions to the nucleic acid molecule comprising the nucleotide sequence, preferably the coding sequence, of SEQ ID NO:1, SEQ ID NO:3, SEQ ID NO:17, SEQ ID NO:19, the cDNA of ATCC 98821, or a complement thereof.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6X sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, SEQ ID NO:3, SEQ ID NO:17, SEQ ID NO:19, the cDNA of ATCC 98821, or the complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the TANGO-69-receptor sequence that may exist in the population, the skilled artisan will further appreciate that changes can be introduced by mutation into the nucleotide sequence of SEQ ID NO:1, SEQ ID NO:3, SEQ ID NO:17, SEQ ID NO:19, or the cDNA of ATCC 98821, thereby leading to changes in the amino acid sequence of the encoded TANGO-69-receptor protein, without altering the biological activity of the TANGO-69-receptor protein. For example, one can make nucleotide substitutions leading to amino acid substitutions at "non-essential" amino acid residues. A "non-essential" amino acid residue is a residue that can be altered from the wild-type sequence of TANGO-69-receptor (e.g., the sequence of SEQ ID NO:2 or SEQ ID NO:18) without altering the biological activity, whereas an "essential" amino acid residue is required for biological activity. For example, amino acid residues that are not conserved or only semi-conserved among TANGO-69-receptor of various species may be non-essential for activity and thus would be likely targets for alteration. Alternatively, amino acid residues that are conserved among the TANGO-69-receptor proteins of various species may be essential for activity and thus would not be likely targets for alteration.

For example, preferred TANGO-69-receptor proteins of the present invention contain at least one cysteine-rich domain in their ligand binding domain. Conservation of cysteine-rich domains is likely to be essential to TANGO-69-receptor activity.

Accordingly, another aspect of the invention pertains to nucleic acid molecules encoding TANGO-69-receptor proteins that contain changes in amino acid residues that are not essential for activity. Such TANGO-69-receptor proteins differ in amino acid sequence from SEQ ID NO:2, SEQ ID NO:4, SEQ ID NO:18, SEQ ID NO:20 yet retain biological activity. In one embodiment, the isolated nucleic acid molecule includes a nucleotide sequence encoding a protein that includes an amino acid sequence that is at least about 66% identical, 70%, 75%, 80%, 85%, 87%, 90%, 92.5%, 95%, 97.5%, 98%, or 99% identical to the amino acid sequence of SEQ ID NO:2, SEQ ID NO:4, SEQ ID NO:18 or SEQ ID NO:20.

An isolated nucleic acid molecule encoding a TANGO-69-receptor protein having a sequence which differs from that of SEQ ID NO:2 or SEQ ID NO:18 can be created by introducing one or more nucleotide substitutions, additions or deletions into the nucleotide sequence of SEQ ID NO:1, SEQ ID NO:3, SEQ ID NO:17, SEQ ID NO:19, the cDNA of ATCC 98821 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in TANGO-69-receptor is preferably replaced with another amino acid residue from the same side chain family. Alternatively, mutations can be introduced randomly along all or part of a TANGO-69-receptor coding sequence, such as by saturation mutagenesis, and the resultant mutants can be screened for TANGO-69-receptor biological activity to identify mutants that retain activity. Following mutagenesis, the encoded protein can be expressed recombinantly and the activity of the protein can be determined.

In a preferred embodiment, a mutant TANGO-69-receptor protein can be assayed for: (1) the ability to form protein-:protein interactions with proteins in the TANGO-69-receptor signalling pathway; (2) the ability to bind a TANGO-69-receptor ligand, e.g., the ability to bind LIGHT/TANGO-69 or LTα; and (3) the ability to interact with mHVEM. In yet another preferred embodiment, a mutant TANGO-69-receptor can be assayed for the ability to modulate cellular proliferation, cellular differentiation, inflammation, viral proliferation, cell death, apoptosis, angiogenesis, and coagulation.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire TANGO-69-receptor coding strand, or to only a portion thereof, e.g., all or part of the protein coding region (or open reading frame). An antisense nucleic acid molecule can be antisense to a noncoding region of the coding strand of a nucleotide sequence encoding TANGO-69-receptor. The noncoding regions ("5' and 3' untranslated regions") are the 5' and 3' sequences which flank the coding region and are not translated into amino acids.

Given the coding strand sequences encoding TANGO-69-receptor disclosed herein (e.g., SEQ ID NO:1, SEQ ID NO:3, SEQ ID NO:17 or SEQ ID NO:19), antisense nucleic acids of the invention can be designed according to the rules of Watson and Crick base pairing. The antisense nucleic acid molecule can be complementary to the entire coding region of TANGO-69-receptor mRNA, but more preferably is an oligonucleotide which is antisense to only a portion of the coding or noncoding region of TANGO-69-receptor mRNA. For example, the antisense oligonucleotide can be complementary to the region surrounding the translation start site of TANGO-69-receptor mRNA, e.g., an oligonucleotide having the sequence ACTCGGACTCCGTACCTC (SEQ ID NO:15) or CGGACTCCGTACCTCGGAGGA (SEQ ID NO:16). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a TANGO-69-receptor protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave TANGO-69-receptor mRNA transcripts to thereby inhibit translation of TANGO-69-receptor mRNA. A ribozyme having specificity for a TANGO-69-receptor-encoding nucleic acid can be designed based upon the nucleotide sequence of a TANGO-69-receptor cDNA disclosed herein (e.g., SEQ ID NO:1, SEQ ID NO:3, SEQ ID NO:17 or SEQ ID NO:19). For example, a derivative of a Tetrahymena L-19 IVS RNA can be constructed in which the nucleotide sequence of the active site is complementary to the nucleotide sequence to be cleaved in a TANGO-69-receptor-encoding mRNA. See, e.g., Cech et al. U.S. Pat. No. 4,987,071; and Cech et al. U.S. Pat. No. 5,116,742. Alternatively, TANGO-69-receptor mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules which form triple helical structures. For example, TANGO-69-receptor gene expression can be inhibited by targeting nucleotide sequences complementary to the regulatory region of the TANGO-69-receptor (e.g., the TANGO-69-receptor promoter and/or enhancers) to form triple helical structures that prevent transcription of the TANGO-69-receptor gene in target cells. See generally Helene (1991) *Anticancer Drug Des.* 6(6) :569–84; Helene (1992) *Ann. N.Y. Acad. Sci.* 660:27–36; and Maher (1992) *Bioassays* 14(12):807–15.

In preferred embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93: 14670–675.

PNAs of TANGO-69-receptor can be used in therapeutic and diagnostic applications. For example, PNAs can be used as antisense or antigene agents for sequence-specific modulation of gene expression by, e.g., inducing transcription or translation arrest or inhibiting replication. PNAs of TANGO-69-receptor can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) *Proc. Natl. Acad. Sci. USA* 93: 14670–675).

In another embodiment, PNAs of TANGO-69-receptor can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of TANGO-69-receptor can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) *Nucleic Acids Res.* 24(17):3357–63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) *Nucleic Acids Res.* 17:5973–88). PNA monomers are then coupled in a stepwise manner to produce a chimeric molecule with a 5' PNA segment and a 3' DNA segment (Finn et al. (1996) *Nucleic Acids Res.* 24(17) :3357–63). Alternatively, chimeric molecules can be synthesized with a 5' DNA segment and a 3' PNA segment (Peterser et al. (1975) *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958–976) or intercalating agents (see, e.g., Zon (1988) *Pharm. Res.* 5:539–549). To this end, the oligonucleotide may be conjugated to another molecule, e.g., a peptide, hybridization triggered cross-linking agent, transport agent, hybridization-triggered cleavage agent, etc.

II. Isolated TANGO-69-receptor Proteins and Anti-TANGO-69-receptor Antibodies

One aspect of the invention pertains to isolated TANGO-69-receptor proteins, and biologically active portions thereof, as well as polypeptide fragments suitable for use as immunogens to raise anti-TANGO-69-receptor antibodies. In one embodiment, native TANGO-69-receptor proteins can be isolated from cells or tissue sources by an appropriate purification scheme using standard protein purification techniques. In another embodiment, TANGO-69-receptor proteins are produced by recombinant DNA techniques. Alternative to recombinant expression, a TANGO-69-receptor protein or polypeptide can be synthesized chemically using standard peptide synthesis techniques.

An "isolated" or "purified" protein or biologically active portion thereof is substantially free of cellular material or other contaminating proteins from the cell or tissue source from which the TANGO-69-receptor protein is derived, or substantially free of chemical precursors or other chemicals when chemically synthesized. The language "substantially free of cellular material" includes preparations of TANGO-69-receptor protein in which the protein is separated from cellular components of the cells from which it is isolated or recombinantly produced. Thus, TANGO-69-receptor protein that is substantially free of cellular material includes preparations of TANGO-69-receptor protein having less than about 30%, 20%, 10%, or 5% (by dry weight) of non-TANGO-69-receptor protein (also referred to herein as a "contaminating protein"). When the TANGO-69-receptor protein or biologically active portion thereof is recombinantly produced, it is also preferably substantially free of culture medium, i.e., culture medium represents less than about 20%, 10%, or 5% of the volume of the protein preparation. When TANGO-69-receptor protein is produced by chemical synthesis, it is preferably substantially free of chemical precursors or other chemicals, i.e., it is separated from chemical precursors or other chemicals which are involved in the synthesis of the protein. Accordingly such preparations of TANGO-69-receptor protein have less than about 30%, 20%, 10%, 5% (by dry weight) of chemical precursors or non-TANGO-69-receptor chemicals.

Biologically active portions of a TANGO-69-receptor protein include peptides comprising amino acid sequences sufficiently identical to or derived from the amino acid sequence of the TANGO-69-receptor protein (e.g., the amino acid sequence shown in SEQ ID NO:2, SEQ ID NO:4, SEQ ID NO:5, SEQ ID NO:18, SEQ ID NO:20 or SEQ ID NO:21), which include fewer amino acids than the full length TANGO-69-receptor proteins, and exhibit at least one activity of a TANGO-69-receptor protein. Typically, biologically active portions comprise a domain or motif with at least one activity of the TANGO-69-receptor protein. A biologically active portion of a TANGO-69-receptor protein can be a polypeptide which is, for example, 10, 25, 50, 100 150, 175 or more amino acids in length. Preferred biologically active polypeptides include one or more identified TANGO-69-receptor structural domains, e.g., the cysteine-rich domains (SEQ ID NO:6; SEQ ID NO:7; SEQ ID NO:8; SEQ ID NO:23, SEQ ID NO:24 or SEQ ID NO:25).

Moreover, other biologically active portions, in which other regions of the protein are deleted, can be prepared by recombinant techniques and evaluated for one or more of the functional activities of a native TANGO-69-receptor protein.

Preferred TANGO-69-receptor protein has the amino acid sequence shown of SEQ ID NO:2 or SEQ ID NO:18. Other useful TANGO-69-receptor proteins are substantially identical to SEQ ID NO:2 or SEQ ID NO:18 and retain the functional activity of the protein of SEQ ID NO:2 or SEQ ID NO:18 yet differ in amino acid sequence due to natural allelic variation or mutagenesis. Accordingly, a useful TANGO-69-receptor protein is a protein which includes an amino acid sequence at least about 66%, 70%, 80%, 85%, 90%, 95%, 97.5%, preferably 98%, 98.5% or 99% identical to the amino acid sequence of SEQ ID NO:2 or SEQ ID NO:18 and retains the functional activity of the TANGO-69-receptor proteins of SEQ ID NO:2 or SEQ ID NO:18. In other instances, the TANGO-69-receptor protein is a protein having an amino acid sequence 66%, 70%, 75%, 80%, 85%, 87%, 90%, 92.5%, 95%, 97.5%, 98%, or 99% identical to a TANGO-69-receptor cysteine-rich domains (SEQ ID NO:6, SEQ ID NO:7, SEQ ID NO:8, SEQ ID NO:23, SEQ ID NO:24, SEQ ID NO:25). In a preferred embodiment, the TANGO-69-receptor protein retains a functional activity of the TANGO-69-receptor protein of SEQ ID NO:2 or SEQ ID NO:18.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions) ×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to TANGO-69-receptor nucleic acid molecules of the invention. BLAST protein searches can be performed with the XBLAST program, score=50, wordlength=3 to obtain amino acid sequences homologous to TANGO-69-receptor protein molecules of the invention. To obtain gapped alignments for comparison purposes, Gapped BLAST can be utilized as described in Altschul et al. (1997) *Nucleic Acids Res.* 25:3389–3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides TANGO-69-receptor chimeric or fusion proteins. As used herein, a TANGO-69-receptor "chimeric protein" or "fusion protein" comprises a TANGO-69-receptor polypeptide operably linked to a non-TANGO-69-receptor polypeptide. A "TANGO-69-receptor polypeptide" refers to a polypeptide having an amino acid sequence corresponding to TANGO-69-receptor, whereas a "non-TANGO-69-receptor polypeptide" refers to a polypeptide having an amino acid sequence corresponding to a protein which is not substantially identical to the TANGO-69-receptor protein, e.g., a protein which is different from the TANGO-69-receptor protein and which is derived from the same or a different organism. Within a TANGO-69-receptor fusion protein the TANGO-69-receptor polypeptide can correspond to all or a portion of a TANGO-69-receptor protein, preferably at least one biologically active portion of a TANGO-69-receptor protein. Within the fusion protein, the term "operably linked" is intended to indicate that the TANGO-69-receptor polypeptide and the non-TANGO-69-receptor polypeptide are fused in-frame to each other. The non-TANGO-69-receptor polypeptide can be fused to the N-terminus or C-terminus of the TANGO-69-receptor polypeptide.

One useful fusion protein is a GST-TANGO-69-receptor fusion protein in which the TANGO-69-receptor sequences are fused to the C-terminus of the GST sequences. Such fusion proteins can facilitate the purification of recombinant TANGO-69-receptor.

In another embodiment, the fusion protein is a TANGO-69-receptor protein containing a heterologous signal sequence at its N-terminus. For example, the native TANGO-69-receptor signal sequence (i.e., about amino acids 1 to 38 of SEQ ID NO:2; SEQ ID NO:5 or about amino acids 1 to 38 of SEQ ID NO:18; SEQ ID NO:21) can be removed and replaced with a signal sequence from another protein. In certain host cells (e.g., mammalian host cells), expression and/or secretion of TANGO-69-receptor can be increased through use of a heterologous signal sequence. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an TANGO-69-receptor-immunoglobulin fusion protein in which all or part of TANGO-69-receptor is fused to sequences derived from a member of the immunoglobulin protein family. The TANGO-69-receptor-immunoglobulin fusion proteins of the invention can be incorporated into pharmaceutical compositions and administered to a subject to inhibit an interaction between a TANGO-69-receptor ligand (e.g., TANGO-69, LIGHT, or LTα) and a TANGO-69-receptor protein on the surface of a cell, to thereby suppress TANGO-69-receptor-mediated signal transduction in vivo. The TANGO-69receptor-immunoglobulin fusion proteins can be used to affect the bioavailability of a TANGO-69-receptor cognate ligand. Inhibition of the TANGO-69-receptor ligand/TANGO-69-receptor interaction may be useful therapeutically, for treating viral proliferation, inflammation and coagulation. Moreover, the TANGO-69-receptor-immunoglobulin fusion proteins of the invention can be used as immunogens to produce anti-TANGO-69-receptor antibodies in a subject, to purify TANGO-69-receptor ligands and in screening assays to identify molecules which inhibit the interaction of TANGO-69-receptor with a TANGO-69-receptor ligand.

Preferably, a TANGO-69-receptor chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). An TANGO-69-receptor-encoding nucleic acid can be cloned into such an expression vector such that the fusion moiety is linked in-frame to the TANGO-69-receptor protein.

The TANGO-69-receptor signal sequence (SEQ ID NO:5) per se can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a nucleic acid sequence encoding a signal sequence of the invention can be operably linked in an expression vector to a protein of interest, such as a protein which is ordinarily not secreted (e.g., a non-signal sequence containing a fragment of a secreted protein) or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

In another embodiment, the signal sequences of the present invention can be used to identify regulatory sequences, e.g., promoters, enhancers, repressors. Since signal sequences are the most amino-terminal sequences of a peptide, it is expected that the nucleic acids which flank the signal sequence on its amino-terminal side will be regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the TANGO-69-receptor proteins (i.e., proteins having a sequence which differs from that of the TANGO-69-receptor amino acid sequence). Such variants can function as either TANGO-69-receptor agonists (mimetics) or as TANGO-69-receptor antagonists. Variants of the TANGO-69-receptor protein can be generated by mutagenesis, e.g., discrete point mutation or truncation of the TANGO-69-receptor protein. An agonist of the TANGO-69-receptor protein can retain substantially the same, or a subset, of the biological activities of the naturally occurring form of the TANGO-69-receptor protein. An antagonist of the TANGO-69-receptor protein can inhibit one or more of the activities of the naturally occurring form of the TANGO-69-receptor protein by, for example, competitively binding to a downstream or upstream member of a cellular signaling cascade which includes the TANGO-69-receptor protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the TANGO-69-receptor proteins.

Variants of the TANGO-69-receptor protein which function as either TANGO-69-receptor agonists (mimetics) or as TANGO-69-receptor antagonists can be identified by screening combinatorial libraries of mutants, e.g., truncation mutants, of the TANGO-69-receptor protein for TANGO-69-receptor protein agonist or antagonist activity. In one embodiment, a variegated library of TANGO-69-receptor variants is generated by combinatorial mutagenesis at the nucleic acid level and is encoded by a variegated gene library. A variegated library of TANGO-69-receptor variants can be produced by, for example, enzymatically ligating a mixture of synthetic oligonucleotides into gene sequences such that a degenerate set of potential TANGO-69-receptor sequences is expressible as individual polypeptides, or alternatively, as a set of larger fusion proteins (e.g., for phage display) containing the set of TANGO-69-receptor sequences therein. There are a variety of methods which can be used to produce libraries of potential TANGO-69-receptor variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential TANGO-69-receptor sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the TANGO-69-receptor protein coding sequence can be used to generate a variegated population of TANGO-69-receptor fragments for screening and subsequent selection of variants of a TANGO-69-receptor protein. In one embodiment, a library of coding sequence fragments can be generated by treating a double stranded PCR fragment of a TANGO-69-receptor coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the TANGO-69-receptor protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of TANGO-69-receptor proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify TANGO-69-receptor variants (Arkin and Yourvan (1992) *Proc. Natl. Acad. Sci. USA* 89:7811–7815; Delgrave et al. (1993) *Protein Engineering* 6(3) :327–331).

An isolated TANGO-69-receptor protein, or a portion or fragment thereof, can be used as an immunogen to generate antibodies that bind TANGO-69-receptor using standard techniques for polyclonal and monoclonal antibody preparation. The full-length TANGO-69-receptor protein can be used or, alternatively, the invention provides antigenic peptide fragments of TANGO-69-receptor for use as immunogens. The antigenic peptide of TANGO-69-receptor comprises at least 8 (preferably 10, 15, 20, or 30) amino acid residues of the amino acid sequence shown in SEQ ID NO:2 or SEQ ID NO:18 and encompasses an epitope of TANGO-69-receptor such that an antibody raised against the peptide forms a specific immune complex with TANGO-69-receptor.

Preferred epitopes encompassed by the antigenic peptide are regions of TANGO-69-receptor that are located on the surface of the protein, e.g., hydrophilic regions. A hydrophobicity analysis of the human TANGO-69-receptor protein sequence (see FIG. 4) indicates the regions that are particularly hydrophilic ,e.g., residue 1 to residue 22 of SEQ ID NO:2; residue 105 to residue 120 of SEQ ID NO:2; and residue 177 to residue 194 of SEQ ID NO:2 and, therefore, are likely to encode surface residues useful for targeting antibody production.

An antigenic TANGO-69-receptor immunogen typically is used to prepare antibodies by immunizing a suitable subject, (e.g., rabbit, goat, mouse or other mammal) with the immunogen. An appropriate immunogenic preparation can contain, for example, antigen recombinantly expressed TANGO-69-receptor protein or a chemically synthesized TANGO-69-receptor polypeptide. The preparation can further include an adjuvant, such as Freund's complete or incomplete adjuvant, or similar immunostimulatory agent. Immunization of a suitable subject with an antigenic TANGO-69-receptor preparation induces a polyclonal anti-TANGO-69-receptor antibody response.

The antigenic peptide of TANGO-69-receptor comprises at least 7 (preferably 10, 15, 20, 30, or more) amino acid residues of TANGO-69-receptor (SEQ ID NO:2 and SEQ ID NO:18), and encompasses at least one epitope of TANGO-69-receptor such that an antibody raised against the peptide forms a specific immune complex with TANGO-69-receptor. Other preferred immunogens include all or a portion (e.g., a portion which comprises at least 7 amino acid residues) of mature TANGO-69-receptor (amino acids 39 to 193 of SEQ ID NO:2; SEQ ID NO:4 or amino acids 39 to 197 of SEQ ID NO:18; SEQ ID NO:20); e.g., amino acids 39–45, 40–46, 41–47, 42–48, 43–49, 44–50, 45–51, 46–52, 47–53, 48–54, 49–55, 50–56, 51–57, 52–58, 53–59, 54–60, 55–61, 56–62, 57–63, 58–64, 59–65, 60–66, 61–67, 62–68, 63–69, 64–70, 65–71, 66–72, 67–73, 68–74, 69–75, 70–76, 71–77, 72–78, 73–79, 74–80, 75–81, 76–82, 77–83, 78–84, 79–85, 80–86, 81–87, 82–88, 83–89, 84–90, 85–91, 86–92, 87–93, 88–94, 89–95, 90–96, 91–97, 92–98, 93–99, 94–100, 95–101, 96–102, 97–103, 98–104, 99–105, 100–106, 101–107, 102–108, 103–109, 104–110, 105–111, 106–112, 107–113, 108–114, 109–115, 110–116, 111–117, 112–118, 113–119, 114–120, 115–121, 116–122, 117–123, 118–124, 119–125, 120–126, 121–127, 122–128, 123–129, 124–130, 125–131, 126–132, 127–133, 128–134, 129–135, 130–136, 131–137, 132–138, 133–139, 134–140, 135–141, 136–142, 137–143, 138–144, 139–145, 140–146, 141–147, 142–148, 143–149, 144–150, 145–151, 146–152, 147–153, 148–154, 149–155, 150–156, 151–157, 152–158, 153–159, 154–160, 155–161, 156–162, 157–163, 158–164, 159–165, 160–166, 161–167, 162–168, 163–169, 164–170, 165–171, 166–172, 167–173, 168–174, 169–175, 170–176, 171–177, 172–178, 173–179, 174–180, 175–181, 176–182, 177–183, 178–184; all or a portion (e.g., a portion which comprises at least 9 amino acid residues) of the C-terminal end of mHVEM1 (amino acid 185 to amino acid 193 of SEQ ID NO:2; e.g., or 179–185, 180–186, 181–187, 182–188, 183–189, 184–190, 185–191, 186–192, 187–193 of SEQ ID NO:2; all or a portion (e.g., a portion which comprises at least 13 amino acid residues of the C-terminal end of mHVEM2, amino acid 185 to amino acid 197 of SEQ ID NO:18); e.g., or 179–185, 180–186, 181–187, 182–188, 183–189, 184–190, 185–191, 186–192, 187–193 of SEQ ID NO:18).

Accordingly, another aspect of the invention pertains to anti-TANGO-69-receptor antibodies. The term "antibody" as used herein refers to immunoglobulin molecules and immunologically active portions of immunoglobulin molecules, i.e., molecules that contain an antigen binding site which specifically binds an antigen, such as TANGO-69-receptor. A molecule which specifically binds to TANGO-69-receptor is a molecule which binds TANGO-69-receptor, but does not substantially bind other molecules in a sample, e.g., a biological sample, which naturally contains TANGO-69-receptor. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind TANGO-69-receptor. The term "monoclonal antibody" or "monoclonal antibody composition", as used herein, refers to a population of antibody molecules that contain only one species of an antigen binding site capable of immunoreacting with a particular epitope of TANGO-69-receptor. A monoclonal antibody composition thus typically displays a single binding affinity for a particular TANGO-69-receptor protein with which it immunoreacts.

Polyclonal anti-TANGO-69-receptor antibodies can be prepared as described above by immunizing a suitable subject with a TANGO-69-receptor immunogen. The anti-TANGO-69-receptor antibody titer in the immunized subject can be monitored over time by standard techniques, such as with an enzyme linked immunosorbent assay (ELISA) using immobilized TANGO-69-receptor. If desired, the antibody molecules directed against TANGO-69-receptor can be isolated from the mammal (e.g., from the blood) and further purified by well-known techniques, such as protein A chromatography to obtain the IgG fraction. At an appropriate time after immunization, e.g., when the anti-TANGO-69-receptor antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985), *Monoclonal Antibodies and Cancer Therapy,* Alan R. Liss, Inc., pp. 77–96) or trioma techniques. The technology for producing hybridomas is well known (see generally *Current Protocols in Immunology* (1994) Coligan et al. (eds.) John Wiley & Sons, Inc., New York, N.Y.). Briefly, an immortal cell line (typically a myeloma) is fused to lymphocytes (typically splenocytes) from a mammal immunized with a TANGO-69-receptor immunogen as described above, and the culture supernatants of the resulting hybridoma cells are screened to identify a hybridoma producing a monoclonal antibody that binds TANGO-69-receptor.

Any of the many well known protocols used for fusing lymphocytes and immortalized cell lines can be applied for the purpose of generating an anti-TANGO-69-receptor monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387–402. Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind TANGO-69-receptor, e.g., using a standard ELISA assay.

Alternative to preparing monoclonal antibody-secreting hybridomas, a monoclonal anti-TANGO-69-receptor antibody can be identified and isolated by screening a recombinant combinatorial immunoglobulin library (e.g., an antibody phage display library) with TANGO-69-receptor to thereby isolate immunoglobulin library members that bind TANGO-69-receptor. Kits for generating and screening phage display libraries are commercially available (e.g., the Pharmacia Recombinant Phage Antibody System, Catalog No. 27–9400–01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J. 12:725–734.

Additionally, recombinant anti-TANGO-69-receptor antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Patent No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141:4053–4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of TANGO-69-receptor. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope.

First, a non-human monoclonal antibody which binds a selected antigen (epitope), e.g., an antibody which inhibits TANGO-69-receptor activity, is identified. The heavy chain and the light chain of the non-human antibody are cloned and used to create phage display Fab fragments. For example, the heavy chain gene can be cloned into a plasmid vector so that the heavy chain can be secreted from bacteria. The light chain gene can be cloned into a phage coat protein gene so that the light chain can be expressed on the surface of phage. A repertoire (random collection) of human light chains fused to phage is used to infect the bacteria which express the non-human heavy chain. The resulting progeny phage display hybrid antibodies (human light chain/non-human heavy chain). The selected antigen is used in a panning screen to select phage which bind the selected antigen. Several rounds of selection may be required to identify such phage. Next, human light chain genes are isolated from the selected phage which bind the selected antigen. These selected human light chain genes are then used to guide the selection of human heavy chain genes as follows. The selected human light chain genes are inserted into vectors for expression by bacteria. Bacteria expressing the selected human light chains are infected with a repertoire of human heavy chains fused to phage. The resulting progeny phage display human antibodies (human light chain/human heavy chain).

Next, the selected antigen is used in a panning screen to select phage which bind the selected antigen. The phage selected in this step display a completely human antibody which recognizes the same epitope recognized by the original selected, non-human monoclonal antibody. The genes encoding both the heavy and light chains are readily isolated and can be further manipulated for production of human antibody. This technology is described by Jespers et al. (1994, *Bio/technology* 12:899–903).

An anti-TANGO-69-receptor antibody (e.g., monoclonal antibody) can be used to isolate TANGO-69-receptor by standard techniques, such as affinity chromatography or immunoprecipitation. An anti-TANGO-69-receptor antibody can facilitate the purification of natural TANGO-69-receptor from cells and of recombinantly produced TANGO-69-receptor expressed in host cells. Moreover, an anti-TANGO-69-receptor antibody can be used to detect TANGO-69-receptor protein (e.g., in a cellular lysate or cell supernatant) in order to evaluate the abundance and pattern of expression of the TANGO-69-receptor protein. Anti-TANGO-69-receptor antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding TANGO-69-receptor (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., TANGO-69-receptor proteins, mutant forms of TANGO-69-receptor, fusion proteins, etc.).

The recombinant expression vectors of the invention can be designed for expression of TANGO-69-receptor in prokaryotic or eukaryotic cells, e.g., bacterial cells such as *E. coli,* insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al. (1988) *Gene* 69:301–315) and pET 11d (Studier et al., *Gene Expression*

Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the TANGO-69-receptor expression vector is a yeast expression vector. Examples of vectors for expression in yeast *S. cerivisae* include pYepSec1 (Baldari et al. (1987) *EMBO J.* 6:229–234), pMFa (Kurjan and Herskowitz, (1982) *Cell* 30:933–943), pJRY88 (Schultz et al. (1987) *Gene* 54:113–123), pYES2 (Invitrogen Corporation, San Diego, Calif.), and pPicZ (InVitrogen Corp, San Diego, Calif.).

Alternatively, TANGO-69-receptor can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166).

Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to TANGO-69-receptor mRNA. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (*Reviews - Trends in Genetics,* Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, TANGO-69-receptor protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding TANGO-69-receptor or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) TANGO-69-receptor protein. Accordingly, the invention further provides methods for producing TANGO-69-receptor protein using the host cells of the invention. In one embodiment, the method comprises culturing the host cell of invention (into which a recombinant expression vector encoding TANGO-69-receptor has been introduced) in a suitable medium such that TANGO-69-receptor protein is produced. In another embodiment, the method further comprises isolating TANGO-69-receptor from the medium or the host cell.

The host cells of the invention can also be used to produce nonhuman transgenic animals. For example, in one embodiment, a host cell of the invention is a fertilized oocyte or an embryonic stem cell into which TANGO-69-receptor-coding sequences have been introduced. Such host cells can then be used to create non-human transgenic animals in which exogenous TANGO-69-receptor sequences have been introduced into their genome or homologous recombinant animals in which endogenous TANGO-69-receptor sequences have been altered. Such animals are useful for studying the function and/or activity of TANGO-69-receptor and for identifying and/or evaluating modulators of TANGO-69-receptor activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous TANGO-69-receptor gene has been altered by homologous recombination between the endogenous gene and an exogenous DNA molecule introduced into a cell of the animal, e.g., an embryonic cell of the animal, prior to development of the animal.

A transgenic animal of the invention can be created by introducing TANGO-69-receptor-encoding nucleic acid into the male pronuclei of a fertilized oocyte, e.g., by microinjection, retroviral infection, and allowing the oocyte to develop in a pseudopregnant female foster animal. The TANGO-69-receptor cDNA sequence e.g., that of (SEQ ID NO:1, SEQ ID NO:3, SEQ ID NO:17, SEQ ID NO:19, the cDNA of ATCC 98821 can be introduced as a transgene into the genome of a non-human animal. Alternatively, a non-human homologue of the human TANGO-69-receptor gene, such as a mouse TANGO-69-receptor gene, can be isolated based on hybridization to the human TANGO-69-receptor cDNA and used as a transgene. Intronic sequences and polyadenylation signals can also be included in the transgene to increase the efficiency of expression of the transgene. A tissue-specific regulatory sequence(s) can be operably linked to the TANGO-69-receptor transgene to direct expression of TANGO-69-receptor protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the TANGO-69-receptor transgene in its genome and/or expression of TANGO-69-receptor mRNA in tissues or cells of the animals. A transgenic founder animal can then be used to breed additional animals carrying the transgene. Moreover, transgenic animals carrying a transgene encoding TANGO-69-receptor can further be bred to other transgenic animals carrying other transgenes.

To create an homologous recombinant animal, a vector is prepared which contains at least a portion of a TANGO-69-receptor gene (e.g., a human or a non-human homolog of the TANGO-69-receptor gene, e.g., a murine TANGO-69-receptor gene) into which a deletion, addition or substitution has been introduced to thereby alter, e.g., functionally disrupt, the TANGO-69-receptor gene. In a preferred embodiment, the vector is designed such that, upon homologous recombination, the endogenous TANGO-69-receptor gene is functionally disrupted (i.e., no longer encodes a functional protein; also referred to as a "knock out" vector). Alternatively, the vector can be designed such that, upon homologous recombination, the endogenous TANGO-69-receptor gene is mutated or otherwise altered but still encodes functional protein (e.g., the upstream regulatory region can be altered to thereby alter the expression of the endogenous TANGO-69-receptor protein). In the homologous recombination vector, the altered portion of the TANGO-69-receptor gene is flanked at its 5' and 3' ends by additional nucleic acid of the TANGO-69-receptor gene to allow for homologous recombination to occur between the exogenous TANGO-69-receptor gene carried by the vector and an endogenous TANGO-69-receptor gene in an embryonic stem cell. The additional flanking TANGO-69-receptor nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced TANGO-69-receptor gene has homologously recombined with the endogenous TANGO-69-receptor gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach,* Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The TANGO-69-receptor nucleic acid molecules, TANGO-69-receptor proteins, and anti-TANGO-69-receptor antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a TANGO-69-receptor protein or anti-TANGO-69-receptor antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In therapeutic applications, anti-TANGO-69-receptor antibodies, like other therapeutic antibodies, are administered parenterally, preferably intravenously or intramuscularly daily, monthly, biweekly, weekly, or more frequently. The preferred dosage is 1.0 mg/kg to 100 mg/kg of body weight, preferably 10 to 20 mg/kg of body weight. Dosages of 50 mg/kg or higher are preferred if the antibody is to be effective within the brain. The preferred dosage for treatment of a particular disorder can be based on results observed with other therapeutic antibodies or it can be determined by one skilled based on testing in animal models. The suitable dosage of antibody in a given situation depends on the disease being treated, the severity of the disease, whether the antibody is being administered for therapeutic or preventative reasons, previous therapies administered, and the patient's clinical history. Treatment is generally continued until the desired therapeutic or preventative effect is observed. Dosage regimes of the type that can be adapted to the methods of the present invention are found in PCT Publication No. WO 94/04188.

Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation is described by Cruikshank et al. ((1997) *J. Acquired Immune Defic. Syndr. Hum. Retrovirol.*, 14:193–203).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). A TANGO-69-receptor protein interacts with other cellular proteins and can thus be used for (i) regulation of cellular proliferation; (ii) regulation of cellular differentiation; (iii) regulation of cell survival, (iv) regulation of inflammation, (v) the regulation of mast cell activity, (vi) regulation of HSV proliferation, and/or (vii) regulation of coagulation. The isolated nucleic acid molecules of the invention can be used to express TANGO-69-receptor protein (e.g., via a recombinant expression vector in a host cell in gene therapy applications), to detect TANGO-69-receptor mRNA (e.g., in a biological sample) or a genetic lesion in a TANGO-69-receptor gene, and to modulate TANGO-69-receptor activity. In addition, the TANGO-69-receptor proteins can be used to screen drugs or compounds which modulate the TANGO-69-receptor activity or expression as well as to treat disorders characterized by insufficient or excessive production of TANGO-69-receptor protein or production of TANGO-69-receptor protein forms which have decreased or aberrant activity compared to TANGO-69-receptor wild type protein. In addition, the anti-TANGO-69-receptor antibodies of the invention can be used to detect and isolate TANGO-69-receptor proteins and modulate TANGO-69-receptor activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to TANGO-69-receptor proteins or have a stimulatory or inhibitory effect on, for example, TANGO-69-receptor expression or TANGO-69-receptor activity.

In one embodiment, the invention provides assays for screening candidate or test compounds which bind to or modulate the activity of the of a TANGO-69-receptor protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other approaches are applicable to peptide, non-peptide oligomer or small molecule libraries of compounds (Lam (1997) *Anticancer Drug Des.* 12:145). Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869) or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

In one embodiment, an assay is a cell-based assay in which a cell which expresses a membrane-associated form of TANGO-69-receptor protein, or a biologically active portion thereof, on the cell surface is contacted with a test compound and the ability of the test compound to bind to a TANGO-69-receptor protein determined. The cell, for example, can be a yeast cell or a cell of mammalian origin. Determining the ability of the test compound to bind to the TANGO-69-receptor protein can be accomplished, for example, by coupling the test compound with a radioisotope or enzymatic label such that binding of the test compound to the TANGO-69-receptor protein or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-associated form of TANGO-69-receptor protein, or a biologically active portion thereof, on the cell surface with a known compound which binds TANGO-69-receptor to form an assay mixture, contacting the assay mixture with a test compound, and determining the ability of the test compound to interact with a TANGO-69-receptor protein, wherein determining the ability of the test compound to interact with a TANGO-69receptor protein comprises determining the ability of the test compound to preferentially bind to TANGO-69-receptor or a biologically active portion thereof as compared to the known compound.

In another embodiment, an assay is a cell-based assay comprising contacting a cell expressing a membrane-associated form of TANGO-69-receptor protein, or a biologically active portion thereof, on the cell surface with a test compound and determining the ability of the test compound to modulate (e.g., stimulate or inhibit) the activity of the TANGO-69-receptor protein or biologically active portion thereof. Determining the ability of the test compound to modulate the activity of TANGO-69-receptor or a biologically active portion thereof can be accomplished, for example, by determining the ability of the TANGO-69-receptor protein to bind to or interact with a TANGO-69-receptor target molecule. As used herein, a "target molecule" is a molecule with which a TANGO-69-receptor protein binds or interacts in nature, for example, a molecule on the surface of a cell which expresses a TANGO-69-receptor protein, a molecule on the surface of a second cell, a molecule in the extracellular milieu, a molecule associated with the internal surface of a cell membrane or a cytoplasmic molecule. A TANGO-69-receptor target molecule can be a non-TANGO-69-receptor molecule or a TANGO-69-receptor protein or polypeptide of the present invention. In one embodiment, a TANGO-69-receptor target molecule is a component of a signal transduction pathway which facilitates transduction of an extracellular signal through the cell membrane and into the cell. The target, for example, can be a second intercellular protein which has catalytic activity or a protein which facilitates the association of downstream signaling molecules with TANGO-69-receptor.

Determining the ability of the TANGO-69-receptor protein to bind to or interact with a TANGO-69-receptor target molecule can be accomplished by one of the methods described above for determining direct binding. In a preferred embodiment, determining the ability of the TANGO-69-receptor protein to bind to or interact with a TANGO-69-receptor target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a TANGO-69-receptor-responsive regulatory element operably linked to a nucleic acid encoding a detectable marker, e.g. luciferase), or detecting a cellular response, for example, cellular differentiation, or cell proliferation.

In yet another embodiment, an assay of the present invention is a cell-free assay comprising contacting a TANGO-69-receptor protein or biologically active portion thereof with a test compound and determining the ability of the test compound to bind to the TANGO-69-receptor protein or biologically active portion thereof. Binding of the test compound to the TANGO-69-receptor protein can be determined either directly or indirectly as described above. In a preferred embodiment, the assay includes contacting the TANGO-69-receptor protein or biologically active portion thereof with a known compound which binds TANGO-69-receptor to form an assay mixture, contacting the assay mixture with a test compound, and determining the ability of the test compound to interact with a TANGO-69-receptor protein, wherein determining the ability of the test compound to interact with a TANGO-69-receptor protein comprises determining the ability of the test compound to preferentially bind to TANGO-69-receptor or biologically active portion thereof as compared to the known compound.

In another embodiment, an assay is a cell-free assay comprising contacting TANGO-69-receptor protein or biologically active portion thereof with a test compound and determining the ability of the test compound to modulate (e.g., stimulate or inhibit) the activity of the TANGO-69-receptor protein or biologically active portion thereof. Determining the ability of the test compound to modulate the activity of TANGO-69-receptor can be accomplished, for example, by determining the ability of the TANGO-69-receptor protein to bind to a TANGO-69-receptor target molecule by one of the methods described above for determining direct binding. In an alternative embodiment, determining the ability of the test compound to modulate the activity of TANGO-69-receptor can be accomplished by determining the ability of the TANGO-69-receptor protein to further modulate a TANGO-69-receptor target molecule. For example, the catalytic/enzymatic activity of the target molecule on an appropriate substrate can be determined as previously described.

In yet another embodiment, the cell-free assay comprises contacting the TANGO-69-receptor protein or biologically active portion thereof with a known compound which binds TANGO-69-receptor to form an assay mixture, contacting the assay mixture with a test compound, and determining the ability of the test compound to interact with a TANGO-69-receptor protein, wherein determining the ability of the test compound to interact with a TANGO-69-receptor protein comprises determining the ability of the TANGO-69-receptor protein to preferentially bind to or modulate the activity of a TANGO-69-receptor target molecule. The cell-free assays of the present invention are amenable to use of both the soluble form and membrane-associated form of TANGO-69-receptor.

In more than one embodiment of the above assay methods of the present invention, it may be desirable to immobilize either TANGO-69-receptor or its target molecule to facilitate separation of complexed from uncomplexed forms of one or both of the proteins, as well as to accommodate automation of the assay. Binding of a test compound to TANGO-69-receptor, or interaction of TANGO-69-receptor with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/TANGO-69-receptor fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or TANGO-69-receptor protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of TANGO-69-receptor binding or activity determined using standard techniques.

Other techniques for immobilizing proteins on matrices can also be used in the screening assays of the invention. For example, either TANGO-69-receptor or its target molecule can be immobilized utilizing conjugation of biotin and streptavidin. Biotinylated TANGO-69-receptor or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with TANGO-69-receptor or target molecules but which do not interfere with binding of the TANGO-69-receptor protein to its target molecule can be derivatized to the wells of the plate, and unbound target or TANGO-69-receptor trapped in the wells by antibody conjugation. Methods for detecting such complexes, in addition to those described above for the GST-immobilized complexes, include immunodetection of complexes using antibodies reactive with the TANGO-69-receptor or target molecule, as well as enzyme-linked assays which rely on detecting an enzymatic activity associated with the TANGO-69-receptor or target molecule.

In another embodiment, modulators of TANGO-69-receptor expression are identified in a method in which a cell is contacted with a candidate compound and the expression of TANGO-69-receptor mRNA or protein in the cell is determined. The level of expression of TANGO-69-receptor mRNA or protein in the presence of the candidate compound is compared to the level of expression of TANGO-69-receptor mRNA or protein in the absence of the candidate compound. The candidate compound can then be identified as a modulator of TANGO-69-receptor expression based on this comparison. For example, when expression of TANGO-69-receptor mRNA or protein is greater (statistically significantly greater) in the presence of the candidate compound than in its absence, the candidate compound is identified as a stimulator of TANGO-69-receptor mRNA or protein expression. Alternatively, when expression of TANGO-69-receptor mRNA or protein is less (statistically significantly less) in the presence of the candidate compound than in its absence, the candidate compound is identified as an inhibitor of TANGO-69-receptor mRNA or protein expression. The level of TANGO-69-receptor mRNA or protein expression in the cells can be determined by methods described herein for detecting TANGO-69-receptor mRNA or protein.

In yet another aspect of the invention, the TANGO-69-receptor proteins can be used as "bait proteins" in a two-hybrid assay or three hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with TANGO-69-receptor ("TANGO-69-receptor-binding proteins" or "TANGO-69-receptor-bp") and modulate TANGO-69-receptor activity. Such TANGO-69-receptor-binding proteins are also likely to be involved in the propagation of signals by the TANGO-69-receptor proteins as, for example, upstream or downstream elements of the TANGO-69-receptor pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, TANGO-69-receptor nucleic acid molecules described herein or fragments thereof, can be used to map the location of TANGO-69-receptor genes on a chromosome. The mapping of the TANGO-69-receptor sequences to chromosomes is an important first step in correlating these sequences with genes associated with disease.

Briefly, TANGO-69-receptor genes can be mapped to chromosomes by preparing PCR primers (preferably 15–25 bp in length) from the TANGO-69-receptor sequences. Computer analysis of TANGO-69-receptor sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the TANGO-69-receptor sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the TANGO-69-receptor sequences to design oligonucleotide primers, sublocalization can be achieved with panels of fragments from specific chromosomes. Other mapping strategies which can similarly be used to map a TANGO-69-receptor sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical, e.g., colcemid, that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., (Human Chromosomes: A Manual of Basic Techniques (Pergamon Press, N.Y., 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the TANGO-69-receptor gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The TANGO-69-receptor sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the TANGO-69-receptor sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The TANGO-69-receptor sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or SEQ ID NO:17 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from TANGO-69-receptor sequences described herein is used to generate a unique identification database for an individual, those same reagents can later be used to identify tissue from that individual. Using the unique identification database, positive identification of the individual, living or dead, can be made from extremely small tissue samples.

3. Use of Partial TANGO-69-receptor Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 or SEQ ID NO:17 are particularly appropriate for this use as greater numbers of polymorphisms occur in the noncoding regions, making it easier to differentiate individuals using this technique. Examples of polynucleotide reagents include the TANGO-69-receptor sequences or portions thereof, e.g., fragments derived from the noncoding regions of SEQ ID NO:1 or SEQ ID NO:17 having a length of at least 20 or 30 bases.

The TANGO-69-receptor sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such TANGO-69-receptor probes can be used to identify tissue by species and/or by organ type.

In a similar fashion, these reagents, e.g., TANGO-69-receptor primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining TANGO-69-receptor protein and/or nucleic acid expression as well as TANGO-69-receptor activity, in the context of a biological sample (e.g., blood, serum, cells, tissue) to thereby determine whether an individual is afflicted with a disease or disorder, or is at risk of developing a disorder, associated with aberrant TANGO-69receptor expression or activity. The invention also provides for prognostic (or predictive) assays for determining whether an individual is at risk of developing a disorder associated with TANGO-69-receptor protein, nucleic acid expression or activity. For example, mutations in a TANGO-69-receptor gene can be assayed in a biological sample. Such assays can be used for prognostic or predictive purpose to thereby prophylactically treat an individual prior to the onset of a disorder characterized by or associated with TANGO-69-receptor protein, nucleic acid expression or activity.

Another aspect of the invention provides methods for determining TANGO-69-receptor protein, nucleic acid expression or TANGO-69-receptor activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of TANGO-69-receptor in clinical trials.

These and other agents are described in further detail in the following sections.

1. Diagnostic Assays

An exemplary method for detecting the presence or absence of TANGO-69-receptor in a biological sample involves obtaining a biological sample from a test subject and contacting the biological sample with a compound or an agent capable of detecting TANGO-69-receptor protein or nucleic acid (e.g., mRNA, genomic DNA) that encodes TANGO-69-receptor protein such that the presence of TANGO-69-receptor is detected in the biological sample. A preferred agent for detecting TANGO-69-receptor mRNA or genomic DNA is a labeled nucleic acid probe capable of hybridizing to TANGO-69-receptor mRNA or genomic DNA. The nucleic acid probe can be, for example, a full-length TANGO-69-receptor nucleic acid, such as the nucleic acid of SEQ ID NO: 1 or 3, or a portion thereof, such as an oligonucleotide of at least 15, 30, 50, 100, 250 or 500 nucleotides in length and sufficient to specifically hybridize under stringent conditions to TANGO-69-receptor mRNA or genomic DNA. Other suitable probes for use in the diagnostic assays of the invention are described herein.

A preferred agent for detecting TANGO-69-receptor protein is an antibody capable of binding to TANGO-69-receptor protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect TANGO-69-receptor mRNA, protein, or genomic DNA in a biological sample in vitro as well as in vivo. For example, in vitro techniques for detection of TANGO-69-receptor mRNA include Northern hybridizations and in situ hybridizations. In vitro techniques for detection of TANGO-69-receptor protein include enzyme linked immunosorbent assays (ELISAs), Western blots, immunoprecipitations and immunofluorescence. In vitro techniques for detection of TANGO-69-receptor genomic DNA include Southern hybridizations. Furthermore, in vivo techniques for detection of TANGO-69-receptor protein include introducing into a subject a labeled anti-TANGO-69-receptor antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting TANGO-69-receptor protein, mRNA, or genomic DNA, such that the presence of TANGO-69-receptor protein, mRNA or genomic DNA is detected in the biological sample, and comparing the presence of TANGO-69-receptor protein, mRNA or genomic DNA in the control sample with the presence of TANGO-69-receptor protein, mRNA or genomic DNA in the test sample.

The invention also encompasses kits for detecting the presence of TANGO-69-receptor in a biological sample (a test sample). Such kits can be used to determine if a subject is suffering from or is at increased risk of developing a disorder associated with aberrant expression of TANGO-69-receptor (e.g., an immunological disorder). For example, the kit can comprise a labeled compound or agent capable of detecting TANGO-69-receptor protein or mRNA in a biological sample and means for determining the amount of TANGO-69-receptor in the sample (e.g., an anti-TANGO-69-receptor antibody or an oligonucleotide probe which binds to DNA encoding TANGO-69-receptor, e.g., SEQ ID NO:1, SEQ ID NO:3, SEQ ID NO:17 or SEQ ID NO:19). Kits may also include instruction for observing that the tested subject is suffering from or is at risk of developing a disorder associated with aberrant expression of TANGO-69-receptor if the amount of TANGO-69-receptor protein or mRNA is above or below a normal level.

For antibody-based kits, the kit can comprise, for example: (1) a first antibody (e.g., attached to a solid support) which binds to TANGO-69-receptor protein; and, optionally, (2) a second, different antibody which binds to TANGO-69-receptor protein or the first antibody and is conjugated to a detectable agent.

For oligonucleotide-based kits, the kit can comprise, for example: (1) an oligonucleotide, e.g., a detectably labelled oligonucleotide, which hybridizes to a TANGO-69-receptor nucleic acid sequence or (2) a pair of primers useful for amplifying a TANGO-69-receptor nucleic acid molecule;

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of TANGO-69-receptor.

2. Prognostic Assays

The methods described herein can furthermore be utilized as diagnostic or prognostic assays to identify subjects having or at risk of developing a disease or disorder associated with aberrant TANGO-69-receptor expression or activity. For example, the assays described herein, such as the preceding diagnostic assays or the following assays, can be utilized to identify a subject having or at risk of developing a disorder associated with TANGO-69-receptor protein, nucleic acid expression or activity, e.g., HSV infection, asthma, delayed hypersensitivity, fibrosis, inflammatory rheumatoid arthritis, or inflammatory bowel disease. Alternatively, the prognostic assays can be utilized to identify a subject having or at risk for developing such a disease or disorder. Thus, the present invention provides a method in which a test sample is obtained from a subject and TANGO-69-receptor protein or nucleic acid (e.g., mRNA, genomic DNA) is detected, wherein the presence of TANGO-69-receptor protein or nucleic acid is diagnostic for a subject having or at risk of developing a disease or disorder associated with aberrant TANGO-69-receptor expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant TANGO-69-receptor expression or activity. For example, such methods can be used to determine whether a subject can be effectively treated with a specific agent or class of agents (e.g., agents of a type which decrease TANGO-69-receptor activity). Thus, the present invention provides methods for determining whether a subject can be effectively treated with an agent for a disorder associated with aberrant TANGO-69-receptor expression or activity in which a test sample is obtained and TANGO-69-receptor protein or nucleic acid is detected (e.g., wherein the presence of TANGO-69-receptor protein or nucleic acid is diagnostic for a subject that can be administered the agent to treat a disorder associated with aberrant TANGO-69-receptor expression or activity).

The methods of the invention can also be used to detect genetic lesions or mutations in a TANGO-69-receptor gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding a TANGO-69-receptor-protein, or the mis-expression of the TANGO-69-receptor gene. For example, such genetic lesions or mutations can be detected by ascertaining the existence of at least one of: 1) a deletion of one or more nucleotides from a TANGO-69-receptor gene; 2) an addition of one or more nucleotides to a TANGO-69-receptor gene; 3) a substitution of one or more nucleotides of a TANGO-69-receptor gene; 4) a chromosomal rearrangement of a TANGO-69-receptor gene; 5) an alteration in the level of a messenger RNA transcript of a TANGO-69-receptor gene; 6) an aberrant modification of a TANGO-69-receptor gene, such as of the methylation pattern of the genomic DNA; 7) the presence of a non-wild type splicing pattern of a messenger RNA transcript of a TANGO-69-receptor gene; 8) a non-wild type level of a TANGO-69-receptor-protein; 9) an allelic loss of a TANGO-69-receptor gene; and 10) an inappropriate post-translational modification of a TANGO-69-receptor-protein. As described herein, there are a large number of assay techniques known in the art which can be used for detecting lesions in a TANGO-69-receptor gene. A preferred biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the TANGO-69-receptor-gene (see, e.g., Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a TANGO-69-receptor gene under conditions such that hybridization and amplification of the TANGO-69-receptor-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a TANGO-69-receptor gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498, 531) can be used to score for the presence of specific mutations by development or loss of a ribozyme cleavage site.

In other embodiments, genetic mutations in TANGO-69-receptor can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). For example, genetic mutations in TANGO-69-receptor can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the TANGO-69-receptor gene and detect mutations by comparing the sequence of the sample TANGO-69-receptor with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the TANGO-69-receptor gene include methods in which protection from cleavage agents is used to detect mismatched bases in RNA/RNA or RNA/DNA heteroduplexes (Myers et al. (1985) *Science* 230:1242). In general, the technique of "mismatch cleavage" entails providing heteroduplexes formed by hybridizing (labeled) RNA or DNA containing the wild-type TANGO-69-receptor sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S1 nuclease to digest mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in TANGO-69-receptor cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994)

*Carcinogenesis* 15:1657–1662). According to an exemplary embodiment, a probe based on a TANGO-69-receptor sequence, e.g., a wild-type TANGO-69-receptor sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in TANGO-69-receptor genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). Single-stranded DNA fragments of sample and control TANGO-69-receptor nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a TANGO-69-receptor gene.

Furthermore, any cell type or tissue, preferably peripheral blood leukocytes, in which TANGO-69-receptor is expressed may be utilized in the prognostic assays described herein.

3. Pharmacogenomics

Agents, or modulators which have a stimulatory or inhibitory effect on TANGO-69-receptor activity (e.g., TANGO-69-receptor gene expression) as identified by a screening assay described herein can be administered to individuals to treat (prophylactically or therapeutically) disorders (e.g., inflammation, coagulation, angiogenesis, HSV proliferation, asthma, dermitits, fibrosis, inflammatory bowel disease, parasitic infections, and viral infections) associated with aberrant TANGO-69-receptor activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of TANGO-69-receptor protein, expression of TANGO-69-receptor nucleic acid, or mutation content of TANGO-69-receptor genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2 ) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of TANGO-69-receptor protein, expression of TANGO-69-receptor nucleic acid, or mutation content of TANGO-69-receptor genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a TANGO-69-receptor modulator, such as a modulator identified by one of the exemplary screening assays described herein.

4. Monitoring of Effects During Clinical Trials

Monitoring the influence of agents (e.g., drugs, compounds) on the expression or activity of TANGO-69-receptor (e.g., the ability to modulate aberrant cell proliferation and/or differentiation) can be applied not only in basic drug screening, but also in clinical trials. For example, the effectiveness of an agent, as determined by a screening assay as described herein, to increase TANGO-69-receptor gene expression, protein levels or protein activity, can be monitored in clinical trials of subjects exhibiting decreased TANGO-69-receptor gene expression, protein levels, or protein activity. Alternatively, the effectiveness of an agent, as determined by a screening assay, to decrease TANGO-69-receptor gene expression, protein levels or protein activity, can be monitored in clinical trials of subjects exhibiting increased TANGO-69-receptor gene expression, protein levels, or protein activity. In such clinical trials, TANGO-69-receptor expression or activity and preferably, that of other genes that have been implicated in for example, a cellular proliferation disorder, can be used as a marker of the immune responsiveness of a particular cell.

For example, and not by way of limitation, genes, including TANGO-69-receptor, that are modulated in cells by treatment with an agent (e.g., compound, drug or small molecule) which modulates TANGO-69-receptor activity (e.g., as identified in a screening assay described herein) can be identified. Thus, to study the effect of agents on cellular proliferation disorders, for example, in a clinical trial, cells can be isolated and RNA prepared and analyzed for the levels of expression of TANGO-69-receptor and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of TANGO-69-receptor or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a TANGO-69-receptor protein, mRNA, or genomic DNA in the preadministration sample; (iii) obtaining one or more post-administration samples from the subject; (iv) detecting the level of expression or activity of the TANGO-69-receptor protein, mRNA, or genomic DNA in the post-administration samples; (v) comparing the level of expression or activity of the TANGO-69-receptor protein, mRNA, or genomic DNA in the pre-administration sample with the TANGO-69-receptor protein, mRNA, or genomic DNA in the post administration sample or samples; and (vi) altering the administration of the agent to the subject accordingly. For example, increased administration of the agent may be desirable to increase the expression or activity of TANGO-69-receptor to higher levels than detected, i.e., to increase the effectiveness of the agent. Alternatively, decreased administration of the agent may be desirable to decrease expression or activity of TANGO-69-receptor to lower levels than detected, i.e., to decrease the effectiveness of the agent.

C. Methods of Treatment

The present invention provides for both prophylactic and therapeutic methods of treating a subject at risk of (or susceptible to) a disorder or having a disorder associated with aberrant TANGO-69-receptor expression or activity. Such disorders include inflammation, angiogenesis, coagulation, proliferation, asthma, fibrosis, inflammatory bowel disease, inflammatory rheumatoid arthritis, parasitic infections, and HSV infection.

1. Prophylactic Methods

In one aspect, the invention provides a method for preventing in a subject, a disease or condition associated with an aberrant TANGO-69-receptor expression or activity, by administering to the subject an agent which modulates TANGO-69-receptor expression or at least one TANGO-69-receptor activity. Subjects at risk for a disease which is caused or contributed to by aberrant TANGO-69-receptor expression or activity can be identified by, for example, any or a combination of diagnostic or prognostic assays as described herein. Administration of a prophylactic agent can occur prior to the manifestation of symptoms characteristic of the TANGO-69-receptor aberrancy, such that a disease or disorder is prevented or, alternatively, delayed in its progression. Depending on the type of TANGO-69-receptor aberrancy, for example, a TANGO-69-receptor agonist or TANGO-69-receptor antagonist agent can be used for treating the subject. The appropriate agent can be determined based on screening assays described herein.

2. Therapeutic Methods

Another aspect of the invention pertains to methods of modulating TANGO-69-receptor expression or activity for therapeutic purposes. The modulatory method of the invention involves contacting a cell with an agent that modulates one or more of the activities of TANGO-69-receptor protein activity associated with the cell. An agent that modulates TANGO-69-receptor protein activity can be an agent as described herein, such as a nucleic acid or a protein, a naturally-occurring cognate ligand of a TANGO-69-receptor protein, a peptide, a TANGO-69-receptor peptidomimetic, or other small molecule. In one embodiment, the agent stimulates one or more of the biological activities of TANGO-69-receptor protein. Examples of such stimulatory agents include active TANGO-69-receptor protein and a nucleic acid molecule encoding TANGO-69-receptor that has been introduced into the cell. In another embodiment, the agent inhibits one or more of the biological activities of TANGO-69-receptor protein. Examples of such inhibitory agents include antisense TANGO-69-receptor nucleic acid molecules and anti-TANGO-69-receptor antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a TANGO-69-receptor protein or nucleic acid molecule. In one embodiment, the method involves administering an agent (e.g., an agent identified by a screening assay described herein), or combination of agents that modulates (e.g., upregulates or downregulates) TANGO-69-receptor expression or activity. In another embodiment, the method involves administering a TANGO-69-receptor protein or nucleic acid molecule as therapy to compensate for reduced or aberrant TANGO-69-receptor expression or activity.

Stimulation of TANGO-69-receptor activity is desirable in situations in which TANGO-69-receptor is abnormally downregulated and/or in which increased TANGO-69-receptor activity is likely to have a beneficial effect. Conversely, inhibition of TANGO-69-receptor activity is desirable in situations in which TANGO-69-receptor is abnormally upregulated and/or in which decreased TANGO-69-receptor activity is likely to have a beneficial effect.

This invention is further illustrated by the following examples which should not be construed as limiting. The contents of all references, patents and published patent applications cited throughout this application are hereby incorporated by reference.

EXAMPLES

Example 1
Isolation and Characterization of Human sHVEM1 and sHVEM2 cDNAs

The cDNAs encoding sHVEM1 and sHVEM2 were identified in a human aortic endothelial cell cDNA library. Human aortic endothelial cells (Clonetics Corporation; San Diego, Calif.) were expanded in culture with Endothelial Cell Growth Media (EGM; Clonetics Corporation) according to the recommendations of the supplier. When the cells reached approximately 80–90% confluence, they were stimulated with TNF (10 ng/ml) and cycloheximide (CHI; 40 micrograms/ml) for 4 hours. Total RNA was isolated using the RNeasy Midi Kit (Qiagen, Inc.; Chatsworth, Calif.), and the poly A+ fraction of total RNA was further purified using Oligotex beads (Qiagen, Inc.). Three micrograms of poly A+ RNA were used to synthesize a cDNA library using the Superscript cDNA Synthesis kit (Gibco BRL, Inc.; Gaithersburg, Md.). Complementary DNA was directionally cloned into the expression plasmid pMET7 using the SalI and NotI sites in the polylinker to construct a plasmid library. Transformants were randomly picked and grown up for single pass sequencing. Complete sequencing of one of the clones revealed an approximately 1.9 kb cDNA insert with a 579 base pair open reading frame predicted to encode a novel 193 amino acid protein, sHVEM1. Complete sequencing of another clone revealed an approximately 1.6 kb cDNA insert cDNA with a 591 base pair reading frame predicted to encode a novel 197 amino acid protein, sHVEM2.

Example 2
Distribution of sHVEM1 mRNA in Human Tissues

The expression of the sHVEM1 gene was analyzed using Northern blot hybridization. Since sHVEM1 and sHVEM2 exhibit high sequence identity, it is expected that the use of a sHVEM1 nucleotide probe will also reveal the pattern of expression of sHVEM2.

The entire gene encoding the sHVEM was used as a probe. The probe was prepared by digesting the pMET7-sHVEM plasmid to excise the full-length sHVEM cDNA. This fragment was radioactively labeled with $^{32}$P-dCTP using the Prime-It kit (Stratagene; La Jolla, Calif.) according to the instructions of the supplier to create a sHVEM1 probe. The sHVEM1 probe was added to filters containing total RNA from human umbilical vein endothelial cells (HUVEC) (Clonetics Corporation, Walkersville, Md.), TNF-stimulated HUVEC cells (were stimulated with 100 ng/ml of TNF for 4 hours), HMC cells (a human mast cell line), and TNF-stimulated HMC cells. The filters were incubated in ExpressHyb hybridization solution (Clontech; Palo Alto, Calif.) and washed at high stringency according to the manufacturer's recommendations.

These studies revealed that sHVEM1 is expressed as an approximately 2 kb transcript in TNF-stimulated and unstimulated HMC cells and in TNF-stimulated HUVECs. Secondary transcripts of 3 kb and 4 kb were also observed in TNF-stimulated HMC cells and unstimulated HMC cells. No sHVEM1 mRNA transcript was observed in unstimulated HUVECs.

Example 3
Characterization of sHVEM1 and sHVEM2 Proteins

In this example, the predicted amino acid sequence of human sHVEM1 protein is compared to amino acid sequences of known proteins and various motifs are identified. In addition, the molecular weight of the human sHVEM1 and sHVEM2 proteins are predicted.

The human sHVEM1 cDNA (FIG. 1; SEQ ID NO:1) isolated as described above encodes a 193 amino acid protein (FIG. 1; SEQ ID NO:2). The signal peptide prediction program SIGNALP Optimized Tool (Nielsen et al. (1997) *Protein Engineering* 10:1–6) predicted that sHVEM1 includes a 38 amino acid signal peptide (amino acid 1 to about amino acid 38 of SEQ ID NO:1; SEQ ID NO:5) preceding the 155 amino acid mature protein (about amino acid 39 to amino acid 193; SEQ ID NO:4).

The human sHVEM2 cDNA (FIG. 5; SEQ ID NO:17) isolated as described above encodes a 197 amino acid protein (FIG. 5; SEQ ID NO:18). The signal peptide prediction program SIGNALP Optimized Tool (Nielsen et al. (1997) *Protein Engineering* 10:1–6) predicted that sHVEM1 includes a 38 amino acid signal peptide (amino acid 1 to about amino acid 38 of SEQ ID NO:18; SEQ ID NO:21) preceding the 159 mature protein (about amino acid 39 to amino acid 197; SEQ ID NO:20).

sHVEM1 and sHVEM2 share high sequence identity. FIG. 7 shows an alignment of the amino acid sequence of sHVEM1 (SEQ ID NO:2) with the amino acid sequence of sHVEM2 (SEQ ID NO:18). FIGS. 6A–6D shows an alignment of the nucleotide sequence of sHVEM1 (SEQ ID NO: 1) with the nucleotide sequence of sHVEM2 (SEQ ID NO: 117). The alignements reveal that sHVEM1 and SHVEM2 exhibit 76.6% sequence identity at the nucleotide level and 93.9% sequence identity at the amino acid level. The proteins are identical from amino acid 1 to amino acid 183 and only differ in sequence from each other at their very C-terminal end. sHVEM has 9 C-terminal amino acids (amino acids 184–193 of SEQ ID NO:2) that are distinct from the 13 amino acids at the C-terminal end of sHVEM2 (amino acids 185–197 of SEQ ID NO:18).

sHVEM1 and sHVEM2 are predicted to be soluble forms of mHVEM and exhibit high sequence identity with the membrane-bound herpesvirus entry mediator (mHVEM), a member of the TNF receptor (TNFR) superfamily. FIG. 3 shows an alignment of the amino acid sequence of sHVEM1 (SEQ ID NO:2) with the amino acid sequence of mHVEM (SEQ ID NO:13) and FIGS. 2A–2D shows an alignment of the nucleotide sequence of sHVEM1 (SEQ ID NO: 1) with the nucleotide sequence of mHVEM (SEQ ID NO: 14). sHVEM1 displays 85.1% nucleotide sequence identity and 65% amino acid sequence identity with mHVEM (FIG. 2 and FIG. 3). However, sHVEM1 and sHVEM2 sequences differ from mHVEM sequence in two main ways. First, sHVEM1 and sHVEM lack the C-terminal end of mHVEM (amino acids 184–283 of SEQ ID NO:13) which contains the transmembrane domain of mHVEM (amino acids 203–225 of SEQ ID NO:13). The absence of a transmembrane domain in sHVEM1 and sHVEM2 suggests that sHVEM1 and sHVEM2 act as soluble receptors. Secondly, sHVEM1 and sHVEM2 have additional amino acids that are not found at the C-terminal end of mHVEM, at their C-terminal ends, e.g., sHVEM1 contains at its C-terminal end an additional 10 amino acids (amino acid 184–193 of SEQ ID NO:2) and sHVEM2 contains at its C-terminal end an additional 14 amino acids (amino acid 184–197). appears to be the soluble form of the mHVEM.

Mature sHVEM1 has a predicted MW of 16.55 kDa (20.76 kDa for immature sHVEM1), not including post-translational modifications. Mature sHVEM2 has a predicted MW of 21.22 kDa (17.0 kDa for the immature sHVEM2).

Example 4

Modulation of LIGHT Binding to mHVEM by TANGO-69-Receptor

Binding assays such as those described by Frankie et al. (1990) *Science* 350:123–135, are performed to determine whether the TANGQ-69-receptor protein modulates the binding of LIGHT to mHVEM. In the binding assay, radiolabelled LIGHT, in the presence and absence of the TANGO-69-receptor, is added to cells expressing the membrane bound mHVEM. The extent to which labelled LIGHT binds mHVEM is evaluated. Briefly, to perform the experiment cells such as CHO-K1 are transfected with mHVEM-expressing plasmid. Radiolabelled LIGHT is first incubated with TANGO-69-receptor and then the mixture is incubated with mHVEM expressing cells. After a predetermined time, cells are washed and unbound radiolabelled LIGHT is removed. The extent to which the radiolabelled LIGHT binds cells is evaluated by direct counting or scintillation counting and compared to the extent to which LIGHT in the absence of TANGO-69-receptor binds the cells.

Binding studies can also be used to test whether the TANGO-69-receptor has the ability to block binding of LTα to mHVEM.

Example 5

Modulation of Herpes Virus Entry by TANGO-69-Receptor Cells

Infectivity assays, such as those described by Montgomery et al., (*Cell*, 87:427–436, 1996) can be used to determine whether TANGO-69-receptor influences the infectivity of HSV. In this infectivity assay, the entry of HSV-1 into cells is evaluated using a recombinant HSV which has an *E. coli* lacZ gene under the control of the HSV-1 ICP4 promoter. Once the HSV enters cells, the expression of β-galactosidase is induced and the amount of β-galactosidase activity is proportional to the amount of virus entering the cells. To perform the experiment, cells such as CHO-K1 are transfected with a mHVEM-expressing plasmid. The cells are then exposed to a mixture of Tango-69-receptor and recombinant HSV. After a predetermined period of time, for example 2 hours, the β-galactosidase activity is quantitated. Quantitation of β-galactosidase can be measured using a β-galactosidase substrate, e.g., o-nitrophenyl β-D-glucopyranide (ONPG, 3 mg/ml). The reaction is monitored by spectrometry at several time points after the addition of ONPG to define the interval over which the generation of product is linear with time (Dynatech ELISA reader). Alternatively, the β-galactosidase substrate X-gal is used. X-gal yields a insoluble blue reaction product. In this case, after infection, cells are fixed, permeabilized and incubated with X-gal.

Example 6

Preparation of TANGO-69-receptor Fusion Proteins

Recombinant TANGO-69-receptor can be produced in a variety of expression systems. For example, the mature TANGO-69-receptor peptide can be expressed as a recombinant glutathione-S-transferase (GST) fusion protein in *E. coli* and the fusion protein can be isolated and characterized. Specifically, as described above, TANGO-69-receptor can be fused to GST and this fusion protein can be expressed in *E. coli* strain PEB199. Expression of the GST-TANGO-69-receptor fusion protein in PEB199 can be induced with IPTG. The recombinant fusion protein can be purified from crude bacterial lysates of the induced PEB199 strain by affinity chromatography on glutathione beads.

Equivalents

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 25

<210> SEQ ID NO 1
<211> LENGTH: 1929
<212> TYPE: DNA
<213> ORGANISM: Homo sapiens
<220> FEATURE:
<221> NAME/KEY: CDS
<222> LOCATION: (297)...(875)

<400> SEQUENCE: 1

```
gtcgacccac gcgtccgctc ggctttgcct ggacagctcc tgcctcccgc agggcccacc      60
tgtgtccccc agcgccgctc cacccagcag gcctgagccc ctctctgctg ccagacaccc     120
cctgctgccc actctcctgc tgctcgggtt ctgaggcaca gcttgtcaca ccgaggcgga     180
ttctctttct ctttctcttt ctcttctggc ccacagccgc agcaatggcg ctgagttcct     240
ctgctggagt tcatcctgct agctgggttc ccgagctgcc ggtctgagcc tgaggc atg     299
                                                                 Met
                                                                   1 gag cct cct gga gac tgg ggg cct cct ccc tgg aga tcc acc ccc aga       347
Glu Pro Pro Gly Asp Trp Gly Pro Pro Pro Trp Arg Ser Thr Pro Arg
            5                  10                  15 acc gac gtc ttg agg ctg gtg ctg tat ctc acc ttc ctg gga gcc ccc       395
Thr Asp Val Leu Arg Leu Val Leu Tyr Leu Thr Phe Leu Gly Ala Pro
         20                  25                  30 tgc tac gcc cca gct ctg ccg tcc tgc aag gag gac gag tac cca gtg       443
Cys Tyr Ala Pro Ala Leu Pro Ser Cys Lys Glu Asp Glu Tyr Pro Val
     35                  40                  45 ggc tcc gag tgc tgc ccc aag tgc agt cca ggt tat cgt gtg aag gag       491
Gly Ser Glu Cys Cys Pro Lys Cys Ser Pro Gly Tyr Arg Val Lys Glu
 50                  55                  60                  65 gcc tgc ggg gag ctg acg ggc aca gtg tgt gaa ccc tgc cct cca ggc       539
Ala Cys Gly Glu Leu Thr Gly Thr Val Cys Glu Pro Cys Pro Pro Gly
                 70                  75                  80 acc tac att gcc cac ctc aat ggc cta agc aag tgt ctg cag tgc caa       587
Thr Tyr Ile Ala His Leu Asn Gly Leu Ser Lys Cys Leu Gln Cys Gln
             85                  90                  95 atg tgt gac cca gcc atg ggc ctg cgc gcg agc cgg aac tgc tcc agg       635
Met Cys Asp Pro Ala Met Gly Leu Arg Ala Ser Arg Asn Cys Ser Arg
        100                 105                 110 aca gag aac gcc gtg tgt ggc tgc agc cca ggc cac ttc tgc atc gtc       683
Thr Glu Asn Ala Val Cys Gly Cys Ser Pro Gly His Phe Cys Ile Val
    115                 120                 125 cag gac ggg gac cac tgc gcc gcg tgc cgc gct tac gcc acc tcc agc       731
Gln Asp Gly Asp His Cys Ala Ala Cys Arg Ala Tyr Ala Thr Ser Ser
130                 135                 140                 145 ccg ggc cag agg gtg cag aag gga ggc acc gag agt cag gac acc ctg       779
Pro Gly Gln Arg Val Gln Lys Gly Gly Thr Glu Ser Gln Asp Thr Leu
                150                 155                 160 tgt cag aac tgc ccc ccg ggg acc ttc tct ccc aat ggg acc ctg gag       827
Cys Gln Asn Cys Pro Pro Gly Thr Phe Ser Pro Asn Gly Thr Leu Glu
            165                 170                 175 gaa tgt cag cac cag acc aac cga gct tgg aaa agt cag aca gac ctc       875
Glu Cys Gln His Gln Thr Asn Arg Ala Trp Lys Ser Gln Thr Asp Leu
        180                 185                 190 tgaggtctca tcctggagct gccaccagcc cagcctccct gggacctgtc ttcactgcct     935
ggggccctgg gagccaggga ggctccctga ggctgagtga acactgggcg ctgcacctgc     995
```

-continued

| | |
|---|---|
| ctctcccacg tcctcggccc cactcccgca ggtgcagctg gctggtgacg aaggccggag | 1055 |
| ctgggaccag cagctcccac tgggtatggt ggtttctctc agggagcctc gtcatcgtca | 1115 |
| ttgtttgctc cacagttggc ctaatcatat gtgtgaaaag aagaaagcca aggggtgatg | 1175 |
| tagtcaaggt gatcgtctcc atccagcgga aaagacagga ggcagaaggt gaggccacag | 1235 |
| tcattgaggc cctgcaggcc cctccggacg tcaccacggt ggccgtggag gagacaatac | 1295 |
| cctcattcac ggggaggagc ccaaaccact gacccacaga ctctgcaccc cgacgccaga | 1355 |
| gatacctgga gcgacggctg ctgaaagagg ctgtccacct ggcgaaacca ccggagcccg | 1415 |
| gaggcttggg ggctccgccc tgggctggct tccgtctcct ccagtggagg gagaggtggg | 1475 |
| gcccctgctg gggtagagct ggggacgcca cgtgccattc ccatgggcca gtgagggcct | 1535 |
| ggggcctctg ttctgctgtg gcctgagctc cccagagtcc tgaggaggag cgccagttgc | 1595 |
| ccctcgctca cagaccacac acccagccct cctgggccag cccagagggc ccttcagacc | 1655 |
| ccagctgtct gcgcgtctga ctcttgtggc ctcagcagga caggccccgg gcactgcctc | 1715 |
| acagccaagg ctggactggg ttggctgcag tgtggtgttt agtggatacc acatcggaag | 1775 |
| tgattttcta aattggattt gaattcggct cctgttttct atttgtcatg aaacagtgta | 1835 |
| tttggggaga tgctgtggga ggatgtaaat atcttgtttc tcctcaaaaa aaaaaaaaa | 1895 |
| aaaaaaaaaa aaaaaaaaaa aaaaaaaaaa aaaa | 1929 |

<210> SEQ ID NO 2
<211> LENGTH: 193
<212> TYPE: PRT
<213> ORGANISM: Homo sapiens

<400> SEQUENCE: 2

Met Glu Pro Pro Gly Asp Trp Gly Pro Pro Trp Arg Ser Thr Pro
 1               5                   10                  15

Arg Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Asn Arg Ala Trp Lys Ser Gln Thr Asp
            180                 185                 190

Leu

-continued

```
<210> SEQ ID NO 3
<211> LENGTH: 579
<212> TYPE: DNA
<213> ORGANISM: Homo sapiens

<400> SEQUENCE: 3
atggagcctc ctggagactg ggggcctcct ccctggagat ccaccccccag aaccgacgtc    60 ttgaggctgg tgctgtatct caccttcctg ggagcccct gctacgcccc agctctgccg   120
tcctgcaagg aggacgagta cccagtgggc tccgagtgct gccccaagtg cagtccaggt   180
tatcgtgtga aggaggcctg cggggagctg acgggcacag tgtgtgaacc ctgccctcca   240
ggcacctaca ttgcccacct caatggccta agcaagtgtc tgcagtgcca aatgtgtgac   300
ccagccatgg gcctgcgcgc gagccggaac tgctccagga cagagaacgc cgtgtgtggc   360
tgcagcccag gccacttctg catcgtccag gacggggacc actgcgccgc gtgccgcgct   420
tacgccacct ccagcccggg ccagagggtg cagaagggag caccgagag tcaggacacc   480 ctgtgtcaga actgcccccc ggggaccttc tctcccaatg ggaccctgga ggaatgtcag   540
caccagacca accgagcttg gaaaagtcag acagacctc                          579

<210> SEQ ID NO 4
<211> LENGTH: 155
<212> TYPE: PRT
<213> ORGANISM: Homo sapiens

<400> SEQUENCE: 4

Leu Pro Ser Cys Lys Glu Asp Glu Tyr Pro Val Gly Ser Glu Cys
 1               5                  10                  15

Pro Lys Cys Ser Pro Gly Tyr Arg Val Lys Glu Ala Cys Gly Glu Leu
                20                  25                  30

Thr Gly Thr Val Cys Glu Pro Cys Pro Pro Gly Thr Tyr Ile Ala His
            35                  40                  45

Leu Asn Gly Leu Ser Lys Cys Leu Gln Cys Gln Met Cys Asp Pro Ala
    50                  55                  60

Met Gly Leu Arg Ala Ser Arg Asn Cys Ser Arg Thr Glu Asn Ala Val
65                  70                  75                  80

Cys Gly Cys Ser Pro Gly His Phe Cys Ile Val Gln Asp Gly Asp His
                85                  90                  95

Cys Ala Ala Cys Arg Ala Tyr Ala Thr Ser Ser Pro Gly Gln Arg Val
            100                 105                 110

Gln Lys Gly Gly Thr Glu Ser Gln Asp Thr Leu Cys Gln Asn Cys Pro
        115                 120                 125

Pro Gly Thr Phe Ser Pro Asn Gly Thr Leu Glu Glu Cys Gln His Gln
    130                 135                 140

Thr Asn Arg Ala Trp Lys Ser Gln Thr Asp Leu
145                 150                 155

<210> SEQ ID NO 5
<211> LENGTH: 38
<212> TYPE: PRT
<213> ORGANISM: Homo sapiens

<400> SEQUENCE: 5

Met Glu Pro Pro Gly Asp Trp Gly Pro Pro Trp Arg Ser Thr Pro
 1               5                  10                  15

Arg Thr Asp Val Leu Arg Leu Val Leu Tyr Leu Thr Phe Leu Gly Ala
                20                  25                  30
```

Pro Cys Tyr Ala Pro Ala
       35

<210> SEQ ID NO 6
<211> LENGTH: 114
<212> TYPE: DNA
<213> ORGANISM: Homo sapiens

<400> SEQUENCE: 6
atggagcctc ctggagactg ggggcctcct ccctggagat ccacccccag aaccgacgtc     60
ttgaggctgg tgctgtatct caccttcctg ggagccccct gctacgcccc agct          114

<210> SEQ ID NO 7
<211> LENGTH: 35
<212> TYPE: PRT
<213> ORGANISM: Homo sapiens

<400> SEQUENCE: 7

Ser Cys Lys Glu Asp Glu Tyr Pro Val Gly Ser Glu Cys Cys Pro Lys
1               5                  10                  15

Cys Ser Pro Gly Tyr Arg Val Lys Glu Ala Cys Gly Glu Leu Thr Gly
            20                  25                  30

Thr Val Cys
        35

<210> SEQ ID NO 8
<211> LENGTH: 44
<212> TYPE: PRT
<213> ORGANISM: Homo sapiens

<400> SEQUENCE: 8

Pro Cys Pro Pro Gly Thr Tyr Ile Ala His Leu Asn Gly Leu Ser Lys
1               5                  10                  15

Cys Leu Gln Cys Gln Met Cys Asp Pro Ala Met Gly Leu Arg Ala Ser
            20                  25                  30

Arg Asn Cys Ser Arg Thr Glu Asn Ala Val Cys Gly
            35                  40

<210> SEQ ID NO 9
<211> LENGTH: 45
<212> TYPE: PRT
<213> ORGANISM: Homo sapiens

<400> SEQUENCE: 9

Cys Ser Pro Gly His Phe Cys Ile Val Gln Asp Gly Asp His Cys Ala
1               5                  10                  15

Ala Cys Arg Ala Tyr Ala Thr Ser Ser Pro Gly Gln Arg Val Gln Lys
            20                  25                  30

Gly Gly Thr Glu Ser Gln Asp Thr Leu Cys Gln Asn Cys
            35                  40                  45

<210> SEQ ID NO 10
<211> LENGTH:
<212> TYPE:
<213> ORGANISM:

<400> SEQUENCE: 10

This Sequence is intentionally skipped

<210> SEQ ID NO 11
<211> LENGTH:

-continued

```
<212> TYPE:
<213> ORGANISM:

<400> SEQUENCE: 11

This Sequence is intentionally skipped

<210> SEQ ID NO 12
<211> LENGTH:
<212> TYPE:
<213> ORGANISM:

<400> SEQUENCE: 12

This Sequence is intentionally skipped

<210> SEQ ID NO 13
<211> LENGTH:
<212> TYPE:
<213> ORGANISM:

<400> SEQUENCE: 13

This Sequence is intentionally skipped

<210> SEQ ID NO 14
<211> LENGTH:
<212> TYPE:
<213> ORGANISM:

<400> SEQUENCE: 14

This Sequence is intentionally skipped

<210> SEQ ID NO 15
<211> LENGTH:
<212> TYPE:
<213> ORGANISM:

<400> SEQUENCE: 15

This Sequence is intentionally skipped

<210> SEQ ID NO 16
<211> LENGTH:
<212> TYPE:
<213> ORGANISM:

<400> SEQUENCE: 16

This Sequence is intentionally skipped

<210> SEQ ID NO 17
<211> LENGTH: 1596
<212> TYPE: DNA
<213> ORGANISM: Homo sapiens

<400> SEQUENCE: 17
gtcgacccac gcgtccggat gaaggaccgc agcaatggcg ctgagttcct ctgctggagt      60
tcatcctgct agctgggttc ccgagctgcc ggtctgagcc tgaggcatgg agcctcctgg     120
agactggggg cctcctccct ggagatccac ccccagaacc gacgtcttga ggctggtgct     180
gtatctcacc tttctgggag cccctgcta cgccccagct ctgccgtcct gcaaggagga     240
cgagtaccca gtgggctccg agtgctgccc caagtgcagt ccaggttatc gtgtgaagga     300
ggcctgcggg gagctgacgg gcacagtgtg tgaaccctgc cctccaggca cctacattgc     360
ccacctcaat ggcctaagca agtgtctgca gtgccaaatg tgtgacccag ccatgggcct     420
```

-continued

| | |
|---|---|
| gcgcgcgagc cggaactgct ccaggacaga gaacgccgtg tgtggctgca gcccaggcca | 480 |
| cttctgcatc gtccaggacg ggaccactg cgccgcgtgc cgcgcttacg ccacctccag | 540 |
| cccgggccag agggtgcaga agggaggcac cgagagtcag gacaccctgt gtcagaactg | 600 |
| cccccegggg accttctctc ccaatgggac cctggaggaa tgtcagcacc agaccaattg | 660 |
| gcctaatcat atgtgtgaaa agaagaaagc caaggggtga gcacacggcg gccccatcag | 720 |
| ggctcatgtc cccagccgtc acctcttgga gctctgtcac cccaagcctg ggaggtggcc | 780 |
| ccagagcttt tccaggatcc gcggctcctc ccagggcagc cactgcaggc tggggcaggt | 840 |
| gatgtagtca aggtgatcgt ctccatccag cggaaaagac aggaggcaga aggtgaggcc | 900 |
| acagtcattg aggccctgca ggcccctccg gacgtcacca cggtggccgt ggaggagaca | 960 |
| ataccctcat tcacggggag gagcccaaac cactgaccca cagactctgc accccgacgc | 1020 |
| cagagatacc tggagcgacg gctgctgaaa gaggctgtcc acctggcgaa accaccggag | 1080 |
| cccggaggct tgggggctcc gccctgggct ggcttccgtc tcctccagtg gagggagagg | 1140 |
| tgggccccct gctggggtag agctggggac gccacgtgcc attcccatgg ccagtgagg | 1200 |
| gcctggggcc tctgttctgc tgtggcctga gctccccaga gtcctgagga ggagcgccag | 1260 |
| ttgcccctcg ctcacagacc acacaccag ccctcctggg ccagcccaga gggcccttca | 1320 |
| gaccccagct gtctgcgcgt ctgactcttg tggcctcagc aggacaggcc ccgggcactg | 1380 |
| cctcacagcc aaggctggac tgggttggct gcagtgtggt gtttagtgga taccacatcg | 1440 |
| gaagtgattt tctaaattgg atttgaattc ggctcctgtt ttctatttgt catgaaacag | 1500 |
| tgtatttggg gagatgctgt gggaggatgt aaatatcttg tttctcctca aaaaaaaaa | 1560 |
| aaaaaaaaaa aaaaaaaaaa aaaaaaaaaa aaaaaa | 1596 |

<210> SEQ ID NO 18
<211> LENGTH: 197
<212> TYPE: PRT
<213> ORGANISM: Homo sapiens

<400> SEQUENCE: 18

```
Met Glu Pro Pro Gly Asp Trp Gly Pro Pro Trp Arg Ser Thr Pro
 1               5                  10                  15
Arg Thr Asp Val Leu Arg Leu Val Leu Tyr Leu Thr Phe Leu Gly Ala
                20                  25                  30
Pro Cys Tyr Ala Pro Ala Leu Pro Ser Cys Lys Glu Asp Glu Tyr Pro
            35                  40                  45
Val Gly Ser Glu Cys Cys Pro Lys Cys Ser Pro Gly Tyr Arg Val Lys
        50                  55                  60
Glu Ala Cys Gly Glu Leu Thr Gly Thr Val Cys Glu Pro Cys Pro Pro
65                  70                  75                  80
Gly Thr Tyr Ile Ala His Leu Asn Gly Leu Ser Lys Cys Leu Gln Cys
                85                  90                  95
Gln Met Cys Asp Pro Ala Met Gly Leu Arg Ala Ser Arg Asn Cys Ser
            100                 105                 110
Arg Thr Glu Asn Ala Val Cys Gly Cys Ser Pro Gly His Phe Cys Ile
        115                 120                 125
Val Gln Asp Gly Asp His Cys Ala Ala Cys Arg Ala Tyr Ala Thr Ser
    130                 135                 140
Ser Pro Gly Gln Arg Val Gln Lys Gly Gly Thr Glu Ser Gln Asp Thr
145                 150                 155                 160
Leu Cys Gln Asn Cys Pro Pro Gly Thr Phe Ser Pro Asn Gly Thr Leu
```

```
                 165                 170                 175
Glu Glu Cys Gln His Gln Thr Asn Trp Pro Asn His Met Cys Glu Lys
            180                 185                 190

Lys Lys Ala Lys Gly
        195

<210> SEQ ID NO 19
<211> LENGTH: 591
<212> TYPE: DNA
<213> ORGANISM: Homo sapiens

<400> SEQUENCE: 19
atggagcctc ctggagactg ggggcctcct ccctggagat ccaccccag aaccgacgtc    60 ttgaggctgg tgctgtatct cacctttctg ggagccccct gctacgcccc agctctgccg   120
tcctgcaagg aggacgagta cccagtgggc tccgagtgct gccccaagtg cagtccaggt   180
tatcgtgtga aggaggcctg cggggagctg acgggcacag tgtgtgaacc ctgccctcca   240
ggcacctaca ttgcccacct caatggccta agcaagtgtc tgcagtgcca aatgtgtgac   300
ccagccatgg gcctgcgcgc gagccggaac tgctccagga cagagaacgc cgtgtgtggc   360
tgcagcccag ccacttctg catcgtccag gacggggacc actgcgccgc gtgccgcgct   420
tacgccacct ccagcccggg ccagagggtg cagaaggag gcaccgagag tcaggacacc   480
ctgtgtcaga actgccccc ggggaccttc tctcccaatg ggaccctgga ggaatgtcag   540
caccagacca attggcctaa tcatatgtgt gaaaagaaga agccaagggg g            591

<210> SEQ ID NO 20
<211> LENGTH: 159
<212> TYPE: PRT
<213> ORGANISM: Homo sapiens

<400> SEQUENCE: 20

Leu Pro Ser Cys Lys Glu Asp Glu Tyr Pro Val Gly Ser Glu Cys Cys
  1               5                  10                  15

Pro Lys Cys Ser Pro Gly Tyr Arg Val Lys Glu Ala Cys Gly Glu Leu
            20                  25                  30

Thr Gly Thr Val Cys Glu Pro Cys Pro Pro Gly Thr Tyr Ile Ala His
        35                  40                  45

Leu Asn Gly Leu Ser Lys Cys Leu Gln Cys Gln Met Cys Asp Pro Ala
    50                  55                  60

Met Gly Leu Arg Ala Ser Arg Asn Cys Ser Arg Thr Glu Asn Ala Val
 65                  70                  75                  80

Cys Gly Cys Ser Pro Gly His Phe Cys Ile Val Gln Asp Gly Asp His
                85                  90                  95

Cys Ala Ala Cys Arg Ala Tyr Ala Thr Ser Ser Pro Gly Gln Arg Val
            100                 105                 110

Gln Lys Gly Gly Thr Glu Ser Gln Asp Thr Leu Cys Gln Asn Cys Pro
        115                 120                 125

Pro Gly Thr Phe Ser Pro Asn Gly Thr Leu Glu Glu Cys Gln His Gln
    130                 135                 140

Thr Asn Trp Pro Asn His Met Cys Glu Lys Lys Lys Ala Lys Gly
145                 150                 155

<210> SEQ ID NO 21
<211> LENGTH: 38
<212> TYPE: PRT
<213> ORGANISM: Homo sapiens
```

<400> SEQUENCE: 21

Met Glu Pro Pro Gly Asp Trp Gly Pro Pro Trp Arg Ser Thr Pro
 1               5                  10                  15

Arg Thr Asp Val Leu Arg Leu Val Leu Tyr Leu Thr Phe Leu Gly Ala
             20                  25                  30

Pro Cys Tyr Ala Pro Ala
         35

<210> SEQ ID NO 22
<211> LENGTH: 114
<212> TYPE: DNA
<213> ORGANISM: Homo sapiens

<400> SEQUENCE: 22
atggagcctc ctggagactg ggggcctcct ccctggagat ccacccccag aaccgacgtc     60
ttgaggctgg tgctgtatct caccttctg ggagccccct gctacgcccc agct           114

<210> SEQ ID NO 23
<211> LENGTH: 35
<212> TYPE: PRT
<213> ORGANISM: Homo sapiens

<400> SEQUENCE: 23

Ser Cys Lys Glu Asp Glu Tyr Pro Val Gly Ser Glu Cys Cys Pro Lys
 1               5                  10                  15

Cys Ser Pro Gly Tyr Arg Val Lys Glu Ala Cys Gly Glu Leu Thr Gly
             20                  25                  30

Thr Val Cys
         35

<210> SEQ ID NO 24
<211> LENGTH: 44
<212> TYPE: PRT
<213> ORGANISM: Homo sapiens

<400> SEQUENCE: 24

Pro Cys Pro Pro Gly Thr Tyr Ile Ala His Leu Asn Gly Leu Ser Lys
 1               5                  10                  15

Cys Leu Gln Cys Gln Met Cys Asp Pro Ala Met Gly Leu Arg Ala Ser
             20                  25                  30

Arg Asn Cys Ser Arg Thr Glu Asn Ala Val Cys Gly
         35                  40

<210> SEQ ID NO 25
<211> LENGTH: 77
<212> TYPE: PRT
<213> ORGANISM: Homo sapiens

<400> SEQUENCE: 25

Cys Ser Pro Gly His Phe Cys Ile Val Gln Asp Gly Asp His Cys Ala
 1               5                  10                  15

Ala Cys Arg Ala Tyr Ala Thr Ser Ser Pro Gly Gln Arg Val Gln Lys
             20                  25                  30

Gly Gly Thr Glu Ser Gln Asp Thr Leu Cys Gln Asn Cys Pro Pro Gly
         35                  40                  45

-continued

```
Thr Phe Ser Pro Asn Gly Thr Leu Glu Glu Cys Gln His Gln Thr Asn
        50                  55                  60
Trp Pro Asn His Met Cys Glu Lys Lys Lys Ala Lys Gly
 65              70                  75
```

What is claimed is:

1. An isolated nucleic acid molecule comprising a nucleotide sequence which encodes a polypeptide comprising the amino acid sequence of SEQ ID NO:2.

2. An isolated nucleic acid molecule comprising a nucleotide sequence which encodes a polypeptide comprising the amino acid sequence of SEQ ID NO:4.

3. An isolated nucleic acid molecule comprising the nucleotide sequence of SEQ ID NO:1.

4. An isolated nucleic acid molecule comprising the nucleotide sequence of SEQ ID NO:3.

5. An isolated nucleic acid molecule comprising a nucleotide sequence which encodes a polypeptide comprising the amino acid sequence of SEQ ID NO:18.

6. An isolated nucleic acid molecule comprising a nucleotide sequence which encodes a polypeptide comprising the amino acid sequence of SEQ ID NO:20.

7. An isolated nucleic acid molecule comprising the nucleotide sequence of SEQ ID NO:17.

8. An isolated nucleic acid molecule comprising the nucleotide sequence of SEQ ID NO:19.

9. The nucleic acid molecule of any of claims 1 to 8 which further comprises vector nucleic acid sequences.

10. The nucleic acid molecule of claim 9, wherein the vector nucleic acid sequences regulate expression of a polypeptide encoded by the nucleic acid molecule.

11. The nucleic acid molecule of any of claims 1 to 8 further comprising nucleic acid sequences encoding a heterologous polypeptide.

12. A host cell which contains the nucleic acid molecule of claim 9.

13. A host cell which contains the nucleic acid molecule of any of claims 1 to 9.

14. The host cell of claim 12 which is a mammalian host cell.

15. The host cell of claim 13 which is a mammalian host cell.

16. A method for producing a polypeptide comprising culturing the host cell of claim 13 under conditions in which the nucleic acid molecule is expressed.

17. The method of claim 16, further comprising isolating the polypeptide from the medium or the host cell.

* * * * *